United States Patent
Raum et al.

(10) Patent No.: US 12,076,181 B2
(45) Date of Patent: Sep. 3, 2024

(54) SYSTEM, METHOD, AND COMPUTER PROGRAM PRODUCT FOR DETERMINING CORTICAL BONE CHARACTERISTICS

(71) Applicant: CHARITÉ—UNIVERSITÄTSMEDIZIN BERLIN, Berlin (DE)

(72) Inventors: Kay Raum, Kleinmachnow (DE); Juan Du, Berlin (DE); Gianluca Iori, Berlin (DE)

(73) Assignee: CHARITÉ—UNIVERSITÄTSMEDIZIN BERLIN, Berlin (DE)

( * ) Notice: Subject to any disclaimer, the term of this patent is extended or adjusted under 35 U.S.C. 154(b) by 535 days.

(21) Appl. No.: 16/624,131

(22) PCT Filed: Jun. 21, 2018

(86) PCT No.: PCT/EP2018/066616
§ 371 (c)(1),
(2) Date: Dec. 18, 2019

(87) PCT Pub. No.: WO2018/234472
PCT Pub. Date: Dec. 27, 2018

(65) Prior Publication Data
US 2020/0129140 A1    Apr. 30, 2020

(30) Foreign Application Priority Data
Jun. 21, 2017    (EP) .................................. 17177198

(51) Int. Cl.
A61B 8/08    (2006.01)
A61B 8/00    (2006.01)

(52) U.S. Cl.
CPC .......... *A61B 8/0875* (2013.01); *A61B 8/4281* (2013.01); *A61B 8/5223* (2013.01)

(58) Field of Classification Search
CPC .... A61B 8/0875; A61B 8/4281; A61B 8/5223
See application file for complete search history.

(56) References Cited

U.S. PATENT DOCUMENTS

| | | | | |
|---|---|---|---|---|
| 5,902,240 A | * | 5/1999 | Ishii | G01N 29/38 600/438 |
| 2005/0004457 A1 | * | 1/2005 | Moilanen | A61B 8/0875 600/437 |

(Continued)

FOREIGN PATENT DOCUMENTS

| CN | 101865931 A | 10/2010 |
|---|---|---|
| CN | 103237501 A | 8/2013 |

(Continued)

OTHER PUBLICATIONS

V. T. Potsika, D. I. Fotiadis, T. Gortsas, G. Iori and K. Raum, "High-frequency cortical backscatter reveals cortical microstructure—A simulation study," 2015 6th European Symposium on Ultrasonic Characterization of Bone, 2015, pp. 1-4 (Year: 205).*

(Continued)

*Primary Examiner* — Boniface N Nganga
(74) *Attorney, Agent, or Firm* — Leason Ellis LLP

(57) ABSTRACT

The present disclosure refers to a system for determining a cortical bone, comprising: an ultrasound transducer which is configured to transmit an ultrasound wave to a region of interest, and to receive a backscattered ultrasound wave which is backscattered from the region of interest, wherein the region of interest comprises a cortical bone; and an evaluation unit which is configured to determine at least one of a pore size, a bone thickness, and a speed of sound in the cortical bone by evaluating the backscattered ultrasound wave. Further, a method for determining a cortical bone is provided. A computer program product which, when executed by a processor, executes the method.

18 Claims, 21 Drawing Sheets

(56) References Cited

U.S. PATENT DOCUMENTS

Figure 1:
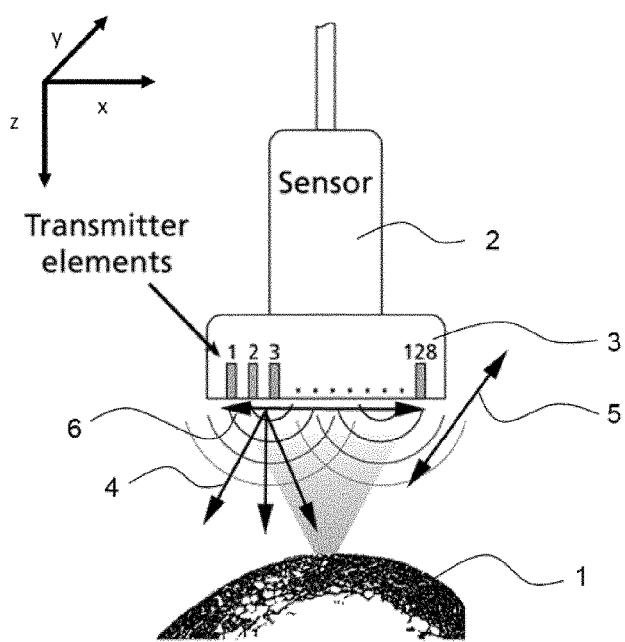

| | | | | |
|---|---|---|---|---|
| 2013/0245443 | A1* | 9/2013 | Karjalainen | A61B 8/5223 600/438 |
| 2015/0211844 | A1* | 7/2015 | Cretin | G01B 17/02 702/171 |

FOREIGN PATENT DOCUMENTS

| | | | |
|---|---|---|---|
| CN | 104619264 | A | 5/2015 |
| CN | 106175838 | A * | 12/2016 |
| JP | 2009153945 | A | 7/2009 |
| JP | 2013537055 | A | 9/2013 |
| KR | 20120055285 | A | 5/2012 |

OTHER PUBLICATIONS

T. Gortsas et al., "The effect of cortical bone porosity on ultrasonic backscattering parameters," 2015 6th European Symposium on Ultrasonic Characterization of Bone, Corfu, Greece, 2015, pp. 1-4, doi: 10.1109 (Year: 2015).*

Chibuzor et al., "Porosity predicted from ultrasound backscatter using multivariate analysis can improve accuracy of cortical bone thickness assessment"J. Acoust. Soc. Am. 141, 575-585 (2017) (Year: 2017).*

Rohde Kerstin et al, "Influence of porosity, pore size, and cortical thickness on the propagation of ultrasonic waves guided through the femoral neck cortex: a simulation study", Feb. 1, 2014 (Feb. 1, 2014), vol. 61, No. 2, p. 302-313.

Malo M K H et al, "Longitudinal elastic properties and porosity of cortical bone tissue vary with age in human proximal femur", Bone, Pergamon Press., Oxford, GB, vol. 53, No. 2, Jan. 17, 2013 (Jan. 17, 2013), p. 451-458.

Hosokawa Atsushi, "Numerical analysis of ultrasound backscattered waves in cancellous bone using a finite-difference time-domain method: isolation of the backscattered waves from various ranges of bone depths", Jun. 1, 2015 (Jun. 1, 2015), vol. 62, No. 6, p. 1201-1210.

Office Action for corresponding CN Application No. 201880041032.2 dated Apr. 19, 2022 (12 pages).

Vassiliki T. Potsika et al., "High-frequency cortical backscatter reveals cortical microstructure-a simulation study", IEEE Explore, Jul. 2015, pp. 1-4.

Office Action for corresponding CN Application No. 201880041032.2 dated Nov. 10, 2022 (40 pages).

Office Action for corresponding EP Application No. 18731471.1 dated Feb. 22, 2024 (6 pages).

* cited by examiner

SYSTEM, METHOD, AND COMPUTER PROGRAM PRODUCT FOR DETERMINING CORTICAL BONE CHARACTERISTICS

CROSS-REFERENCE TO RELATED APPLICATIONS

This application is a U.S. National Stage Application under 35 U.S.C. § 371 of International Patent Application No. PCT/EP2018/066616, filed Jun. 21, 2018 which claims priority to European Patent Application No. 17177198.3, filed Jun. 21, 2017, the contents of which are each hereby incorporated by reference in their respective entireties.

The disclosure relates to a system, a method, and a computer program product for determining a cortical bone.

BACKGROUND

Osteoporosis (OP) is one of the most important global health problems of aging populations which increases the risk of bone fractures, reduces mobility and quality of life, and increases mortality. The annual economic burden of incident and prior fragility fractures was estimated at € 37 billion and the costs are expected to increase by 25% in 2025. Age related OP and other degenerative bone pathologies are caused by an imbalance between bone resorption and bone formation, leading to a rarefication of trabecular bone and to thinning and increased porosity of cortical bone. The clinical evaluation of bone is mainly done using a single scalar parameter, i.e., areal bone mineral density (BMD) by low-resolution X-ray projection imaging modalities (DXA: dual energy X-ray absorptiometry) and risk factors, e.g., age, gender, family history, ethnicity, life style, medications.

Although BMD is until now the single most important predictor of osteoporotic fractures in postmenopausal women without a previous fracture, the majority of fractures occurs without a significant reduction in BMD. Particularly dramatic is the situation for individuals with low or moderate BMD (T-score>−2.0), who sustain a fragility fracture. Current diagnostic and treatment guidelines prevent at least 80% of these individuals from receiving therapies to reduce the risk of future fractures. This "treatment gap" varies in European countries between 25% in Spain and 95% in Bulgaria. Therefore, OP is one of the most underdiagnosed diseases in Europe.

As mentioned above, osteoporosis and fracture risk are currently indirectly assessed by the measurement of BMD by DXA. Except for the recently introduced clinical high-resolution peripheral QCT scanners (HRpQCT: High-Resolution peripheral Computed Tomography), cortical bone loss caused by an increase of cortical pore dimensions is poorly captured by X-ray based techniques. Current international, European and national guidelines for the assessment of osteoporotic fracture risk and the therapeutic management of patients mostly rely on the measurement of BMD and assessment of clinical risk factors. The guidelines advocate treatment in patients with established osteoporosis (i.e., a T-score≤−2.5 at the femoral neck, total hip or lumber spine and/or a vertebral fracture with a height loss>25%). Cortical thickness and large cortical pores (i.e., 120 μm) can be measured in-vivo by means of HRpQCT. However, this technique is anticipated to remain a clinical research tool due to the small investigation volume, applied radiation dose, high cost and low availability of the system.

Changes in cortical bone porosity measured by HRpQCT has already demonstrated diagnostic sensitivity in osteopenic (i.e., the underdiagnosed population), but not in osteoporotic women. Clinical studies using HRpQCT revealed that cortical bone porosity is a major risk factor for fracture independent of BMD and FRAX (Fracture Risk Assessment Tool) and improves identification of women with fracture risk. Age-related losses of cortical bone and increases in cortical porosity were shown to have a much larger role than previously recognized, and increased cortical porosity might characterize patients at increased risk of fragility fractures. Additionally, not only average porosity but also pore size and local accumulation of large basic multicellular units (BMUs) have been associated with a reduction of the hip strength. HRpCT is restricted to a few clinical research centers worldwide, peripheral skeletal sites and uses ionizing radiation.

Various quantitative ultrasound technologies (QUS) also aim at approximating the properties mentioned above. However, the success of these approaches is hampered by i) the lack of image guidance, ii) operator dependency, iii) the complex and irregular cortical bone structure causing non-trivial interpretation of data, and iv) the need for dedicated equipment.

One method that targets cortical bone is the so-called axial transmission method. The principle of this method is to use pairs of ultrasound transmitters and receivers. The former emit waves through the skin to the bone surface. Various wave modes are coupled into the cortical bone shell, which travel along the longitudinal bone direction. Waves coupled back to the soft tissue are recorded by the receiver. Initial versions of this method determined the velocity of the first arriving signal, which depends on cortical thickness, matrix stiffness and porosity. Later developed versions, as described in documents US 2005/0004457 A1 and US 2016/0161450 A1, aim at the measurement of dispersive waves, from which bulk properties, such as cortical thickness and stiffness are estimated. However, the drawbacks of this approach are that it requires i) dedicated hardware, ii) fitting a theoretical model to the detected wave modes, and iii) various model assumptions about the cortical bone shape and a tissue model to estimate porosity.

Document US 2008/0125653 A1 discloses a method and a system for determining bone properties using ultrasonic sound. In particular, an average porosity of cancellous bone is determined by analyzing parameters of the ultrasonic sound backscattered from the bone.

The document Karjalainen J P et al, *Multi-site bone ultrasound measurements in elderly women with and without previous hip fractures*, Osteoporos Int., 2012, discloses a method which targets cortical bone and employs a single element focused transducer. This method assumes a constant, predefined speed of sound in bone (3565 m/s) and calculates a cortical thickness index by multiplying the time lag between the ultrasound echoes from the peri- and endosteum of the cortex with it. The thickness index is affected by porosity and matrix transverse stiffness in addition the cortical thickness.

The document Eneh, C T M et al., *Porosity predicted from ultrasound backscatter using multivariate analysis can improve accuracy of cortical bone thickness assessment*, JASA, 2017, discloses an empirical method for predicting porosity ex-vivo in cubes extracted from cortical bone using ultrasound backscatter generated by single-element focused ultrasound probes at 2.25 and 5 MHz.

The document Rohde, K et al., *Influence of porosity, pore size, and cortical thickness on the propagation of ultrasonic waves guided through the femoral neck cortex: a simulation study*, IEEE UFFC, 2014, discloses a guided wave through-transmission simulation study investigating the effects of cortical microstructural changes on the propagation travel time of low-frequency waves from 175 kHz to 825 kHz. In the document it is concluded that using this approach, the estimation of the cortical pore diameter seems to be difficult or unrealistic in-vivo.

In another method, originally developed for acoustic microscopy, the refraction of focused sound fields at the soft tissue-bone interface to estimate the speed of sound and thickness of a bone by a multi-focus measurement is employed. The document Wydra, A et al., *Development of a practical ultrasonic approach for simultaneous measurement of the thickness and the sound speed in human skull bones: a laboratory phantom study*, PhysMedBiol, 2013, discloses a phantom study to demonstrate the feasibility of this approach in human skull bones. In contrast to cortical bone of the peripheral skeleton, skull bone is relatively thick (about 7 to 10 mm), has regular boundaries and a different microstructure. Moreover, the method requires direct contact of the transducer array to the skull bone surface.

SUMMARY

It is an object to provide improved technology for determining bone properties or characteristics.

A system according to claim 1, a method according to claim 14, and a computer program product according to claim 15 are provided. Further embodiments are subject matter of dependent claims.

In one aspect, a system for determining a cortical bone is disclosed. The system comprises an ultrasound transducer and an evaluation unit. The ultrasound transducer is configured to transmit an ultrasound wave to a region of interest, and to receive a backscattered ultrasound wave which is backscattered from the region of interest. The region of interest comprises or is provided on a cortical bone. The evaluation unit is configured to determine, for the cortical bone, at least one of a pore size, a bone thickness (a cortical bone thickness), and speed of sound in the cortical bone by evaluating the backscattered ultrasound wave. The ultrasound transducer may be configured to transmit ultrasound waves in and receive backscattered ultrasound waves from a three-dimensional volume in the region of interest.

In another aspect, a method for determining a cortical bone is provided. The method comprises transmitting, by an ultrasound transducer, an ultrasound wave to a region of interest, receiving, by the ultrasound transducer, an ultrasound wave which is backscattered from the region of interest, wherein the region of interest comprises a cortical bone, and determining, by an evaluation unit, at least one of a pore size, a bone thickness, and speed of sound in the cortical bone by evaluating the backscattered ultrasound waves.

Also, a computer program product is disclosed. The computer program product, when executed by a processor, executes the method for determining a pore size, a bone thickness, and speed of sound of the cortical bone. The computer program product may be provided on a non-transitory storage medium.

With regard to speed of sound and bone thickness, it may be provided that the evaluation unit is configured, alternatively or in addition, to evaluate ultrasound refraction-based relationships for determining to at least one of speed of sound and bone thickness in the cortical bone. The evaluation unit may be configured to determine confocal positions and travel time delay of front and back-side reflections of the ultrasound wave for each of a plurality of scan positions, and determine at least one of the speed of sound and the bone thickness using the ultrasound refraction-based relationships. With respect to determining at least one of bone thickness and speed of sound in the cortical bone by evaluating the backscattered ultrasound wave, such procedure comprising determining confocal positions and travel time delay of front and back-side reflections may be applied alternatively or in addition.

In one embodiment, the system and the method may be implemented using conventional 3D medical ultrasound scanner technology (which is the most widely distributed 3D diagnostic imaging technology) in combination with a dedicated data acquisition/analysis scheme to derive cortical bone characteristics such as an average pore dimension non-invasively without ionizing radiation from spectral analysis of high-frequency backscattered waves. It allows a spatially resolved assessment of at least one of the pore size, bone thickness, and speed of sound of I in the cortical bone. Each of such characteristics of the cortical bone may provide an early indicator of OP related changes in bone remodeling.

The ultrasound transducer may comprise an array of ultrasound transducer units, wherein each ultrasound transducer unit is configured to transmit an ultrasound wave and to receive a backscattered ultrasound wave. The array of ultrasound transducer units may comprise more than two ultrasound transducer units. In one embodiment, the array of ultrasound transducer units may comprise 128 ultrasound transducer units.

The array may be a one-dimensional (1D) array. The ultrasound transducer units may be arranged in a line or in a curve. In this case, the array may be connected to i) a translation stage or ii) a position tracking system, which enable positioning in the direction perpendicular to the array. Alternatively, the array may be a two-dimensional (2D) array. In another embodiment, a single transducer or pairs of transducers may be employed, which may be connected to a scanning system to allow positioning and steering of transmitted and received ultrasound beams.

The system may further comprise a control unit which is configured to control a position, a direction, a transmit frequency, and/or a focus depth of the ultrasound wave.

The ultrasound transducer unit may further be configured to receive several backscattered ultrasound waves, wherein the backscattered ultrasound waves are received for each ultrasound transducer unit individually.

The ultrasound transducer unit may further be configured to focus the transmitted ultrasound wave(s) at variable distances.

The evaluation unit may further be configured to detect an outer bone surface of the cortical bone.

The evaluation unit may further be configured to determine a reference spectrum from ultrasound waves backscattered at normal incidence.

The evaluation unit may further be configured to calculate a depth-dependent normalized backscatter spectrum.

The evaluation unit may further be configured to determine characteristic parameters from the depth-dependent normalized backscatter spectrum, e.g., an apparent integrated backscatter (AIB) amplitude or frequency and depth-dependent features of the normalized backscatter spectrum. The latter may be used to estimate sound attenuation, an attenuation-corrected backscatter spectrum, or depth-dependent variations of the backscatter caused by anatomical variations of the pore size and pore density.

The evaluation unit may further be configured to calculate a pulse travel time delay between signals reflected at outer and inner bone boundaries.

The evaluation unit may further be configured to calculate the speed of sound and thickness of cortical bone from a focus-dependent variation of amplitudes of bone front and back-side reflections and the pulse travel time delay between the amplitudes of bone front and back-side reflections.

The ultrasound wave(s) may have frequencies in the range between 1 MHz and 10 MHz.

The evaluation unit may comprise a processor and memory.

The features disclosed with regard to the system can also be applied to the method and vice versa.

DESCRIPTION OF EMBODIMENTS

Figure 2:
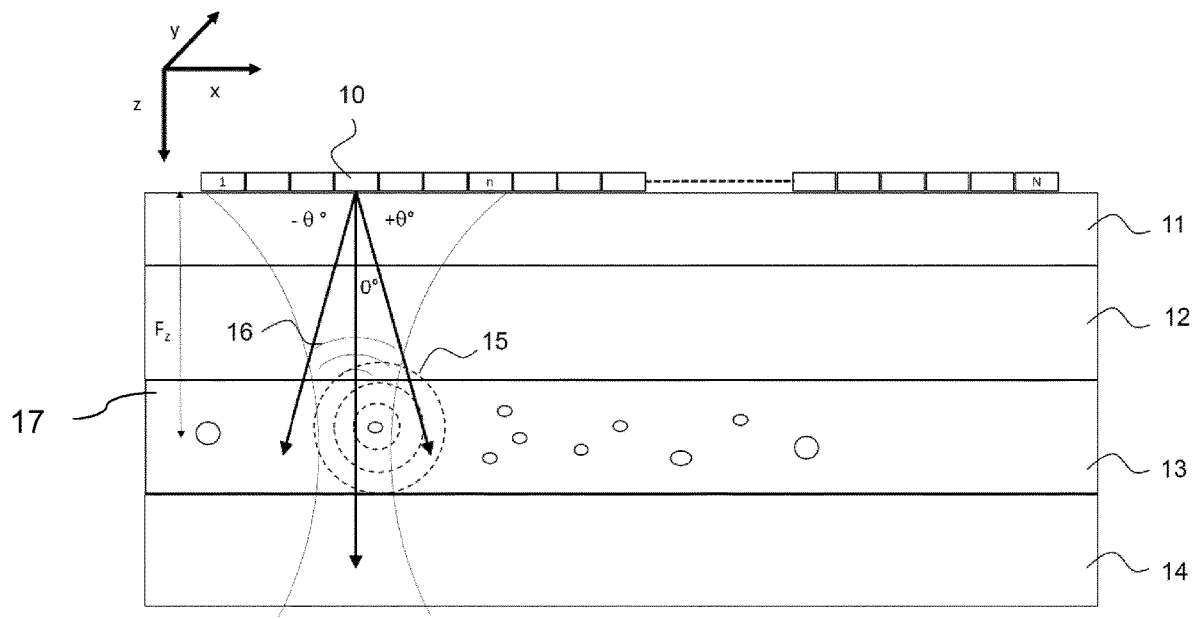
Figure 3:
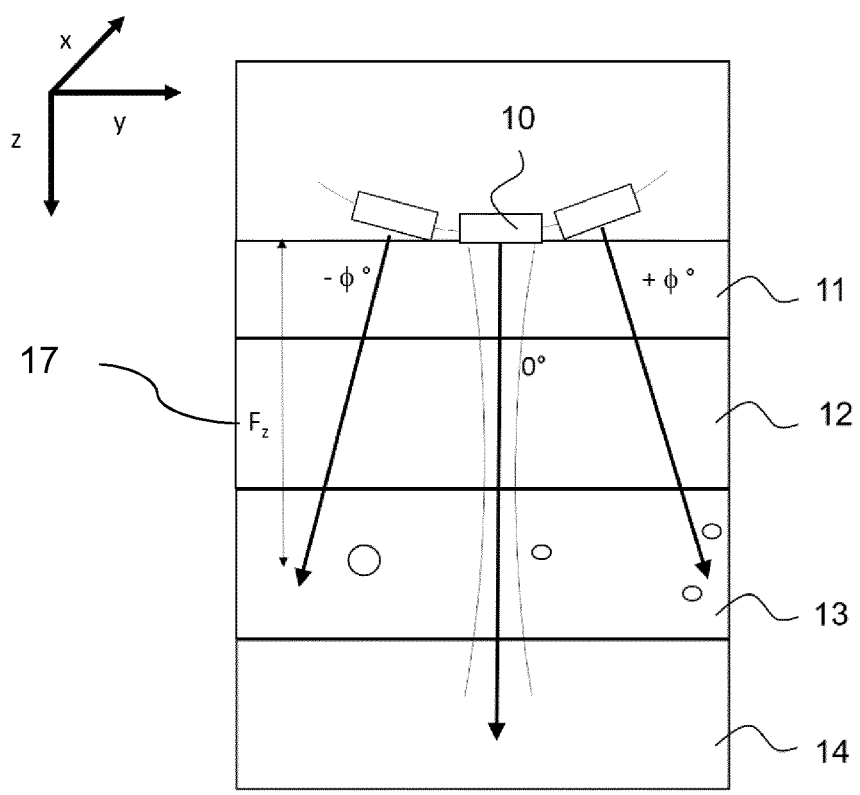
Figure 4:
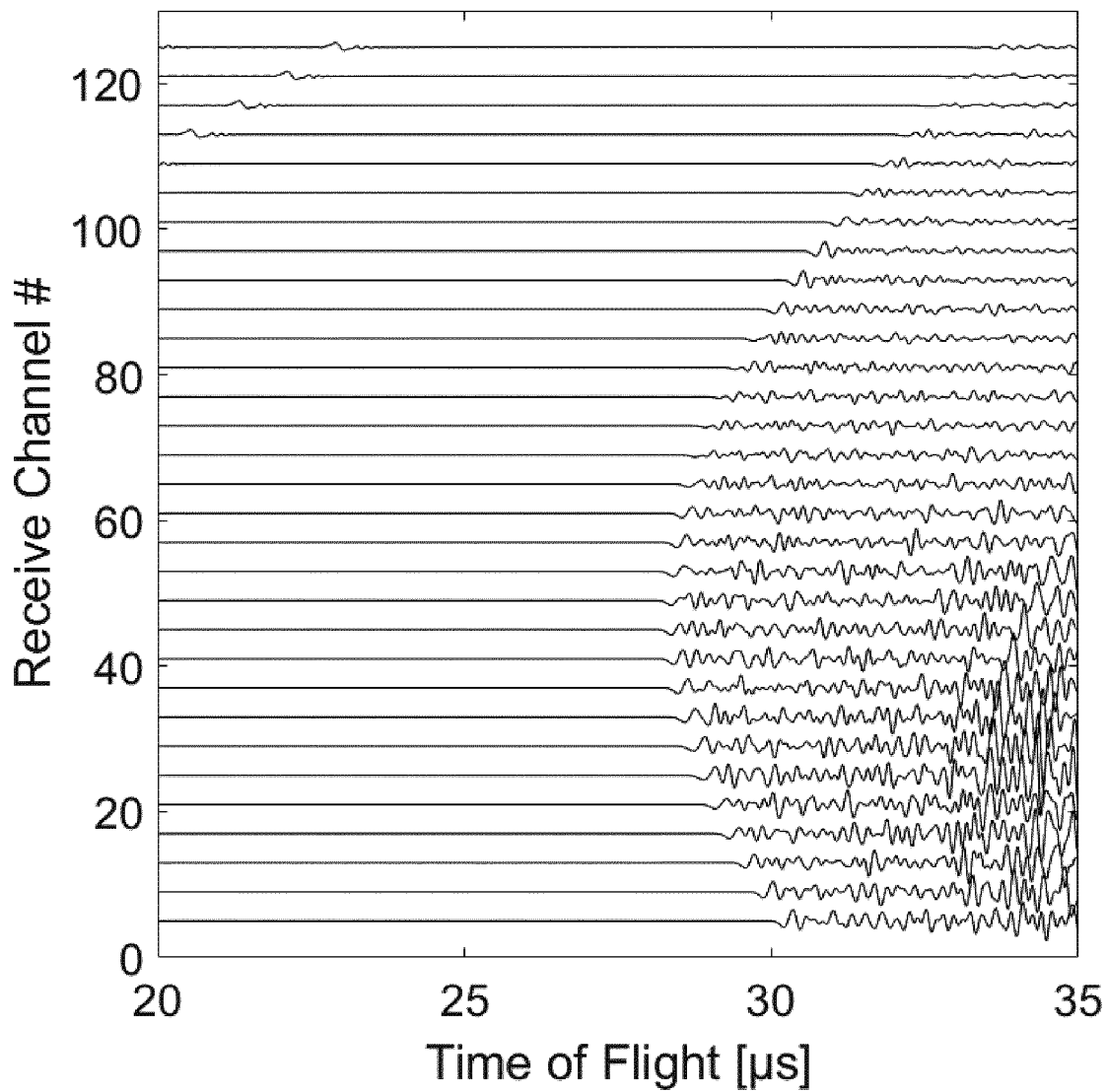
Figure 5:
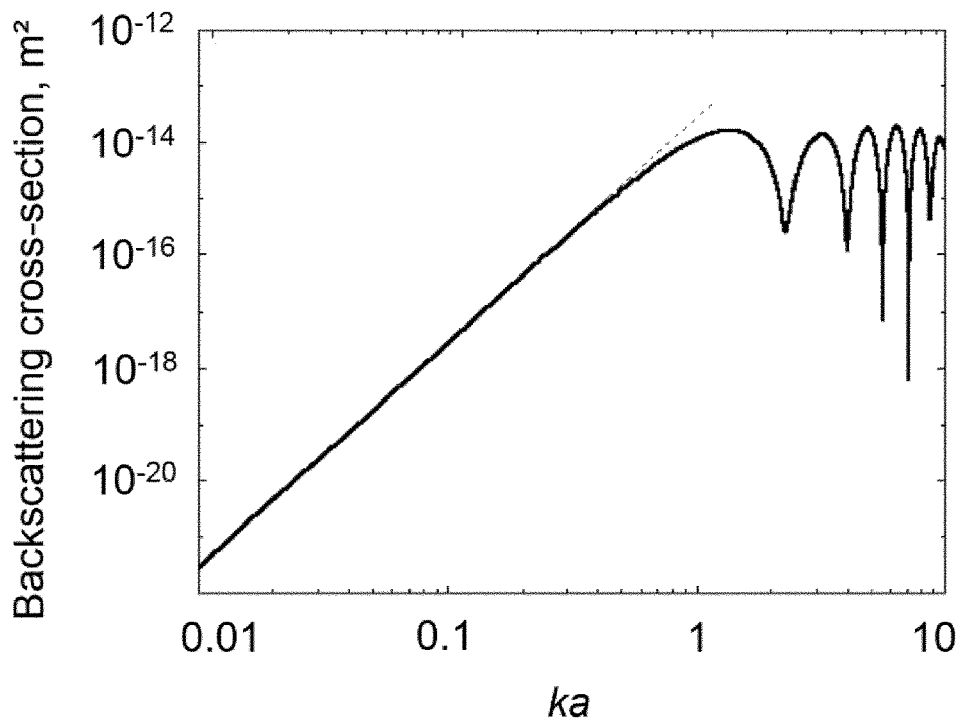
Figure 6:
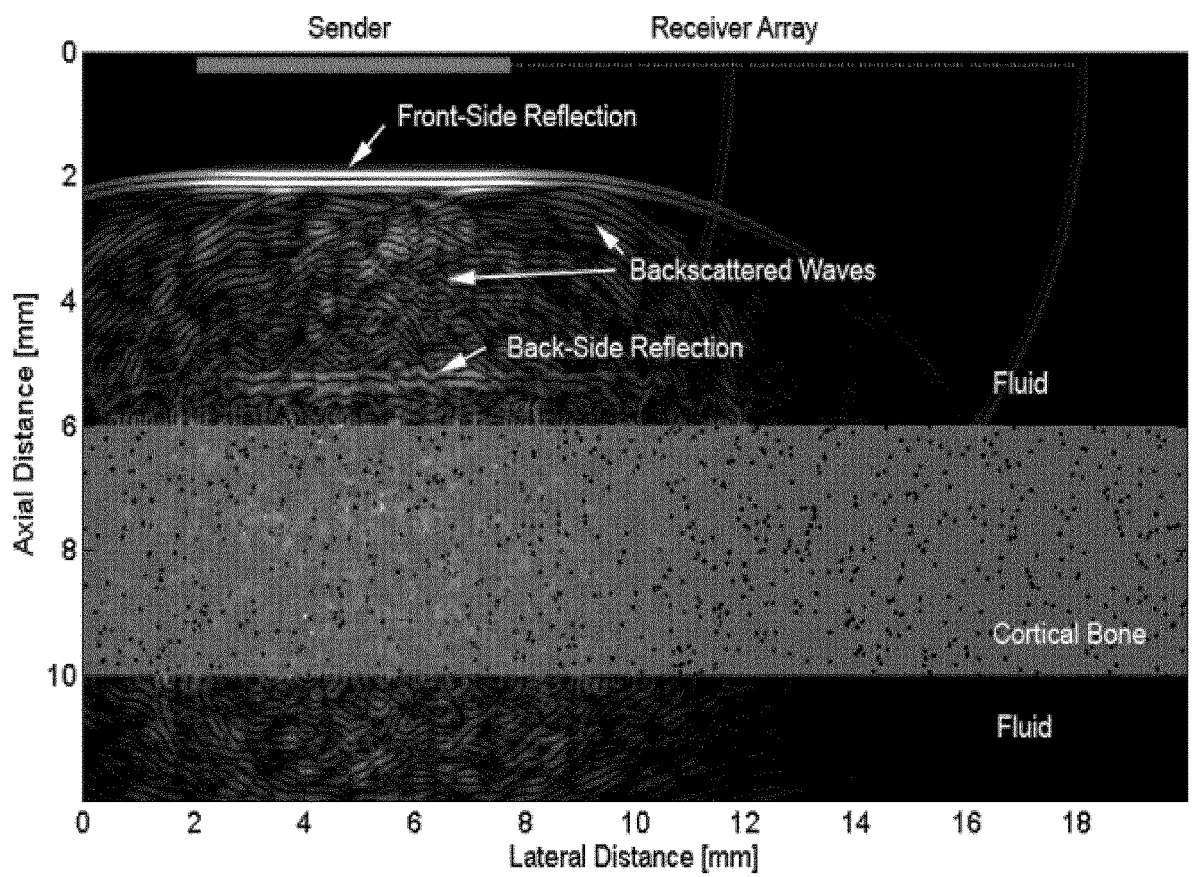
Figure 7:
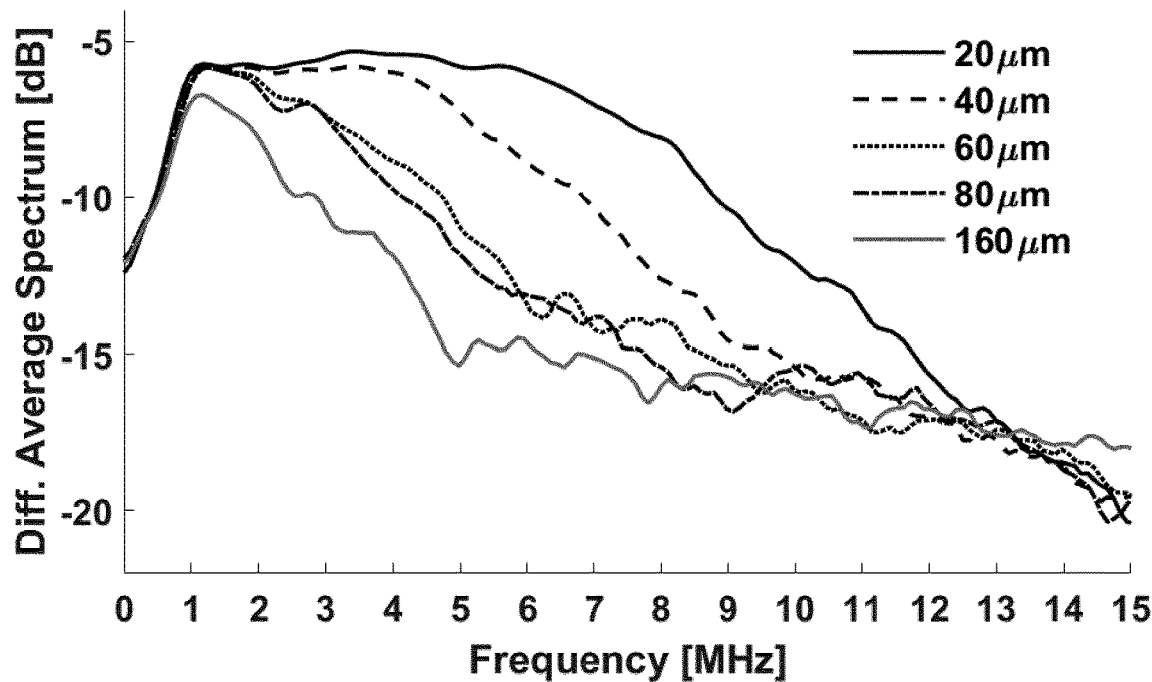
Figure 8:
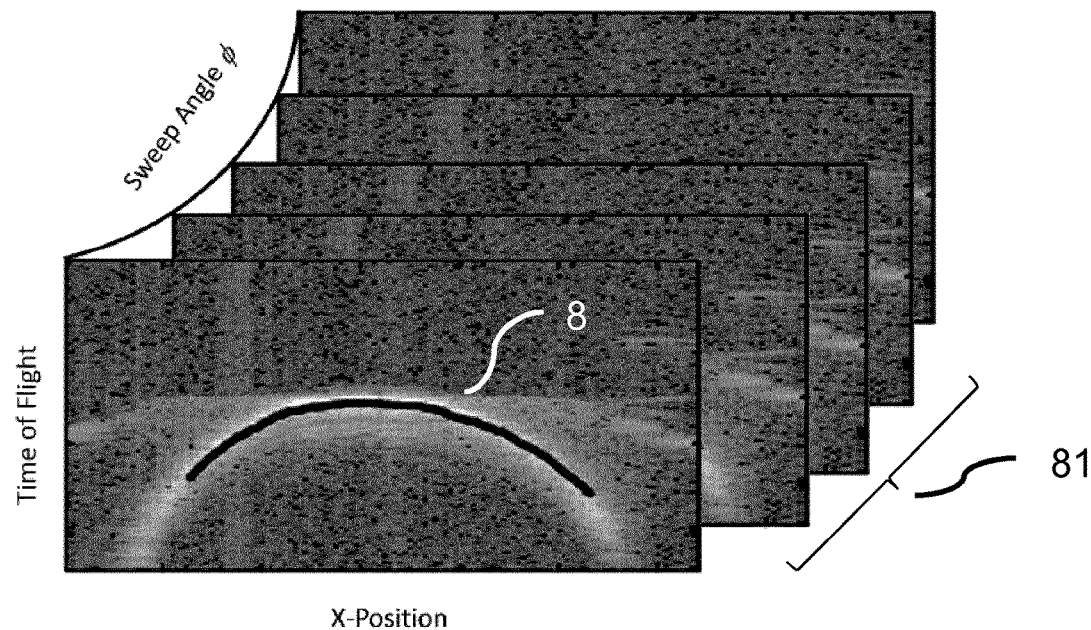
Figure 9:
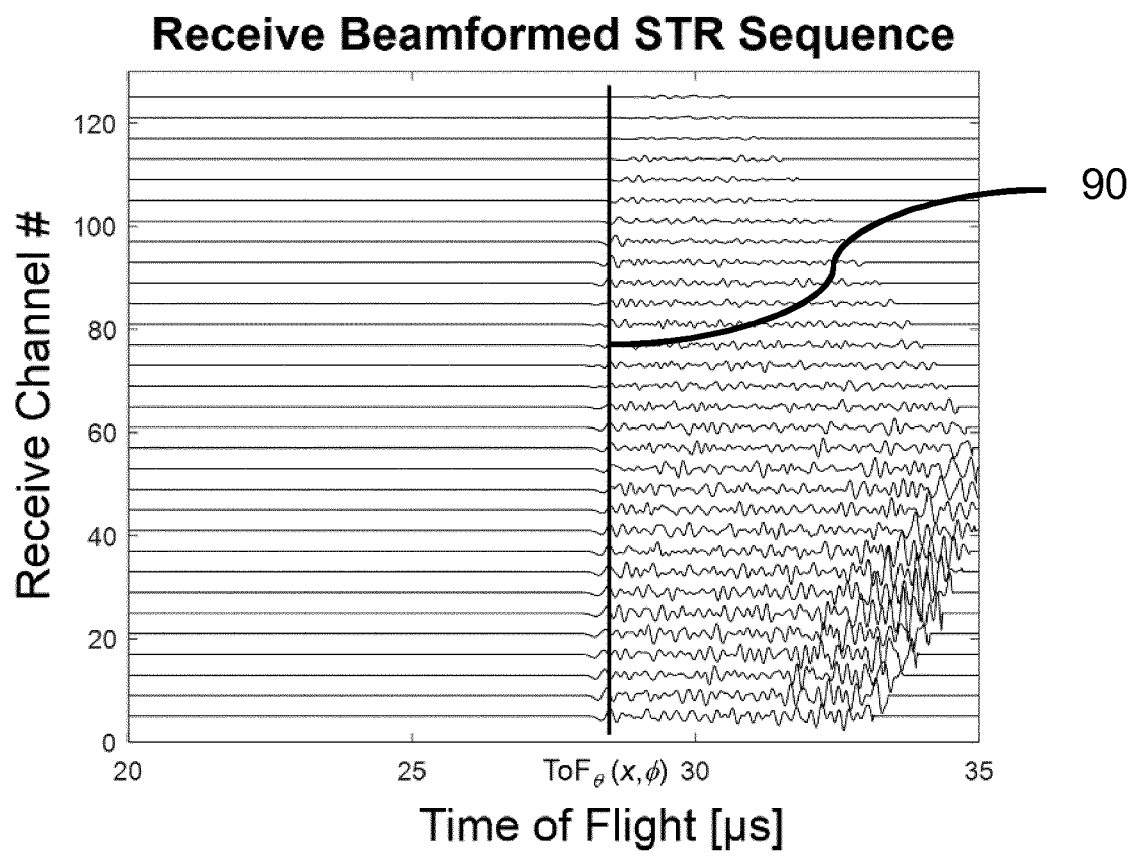
Figure 10:
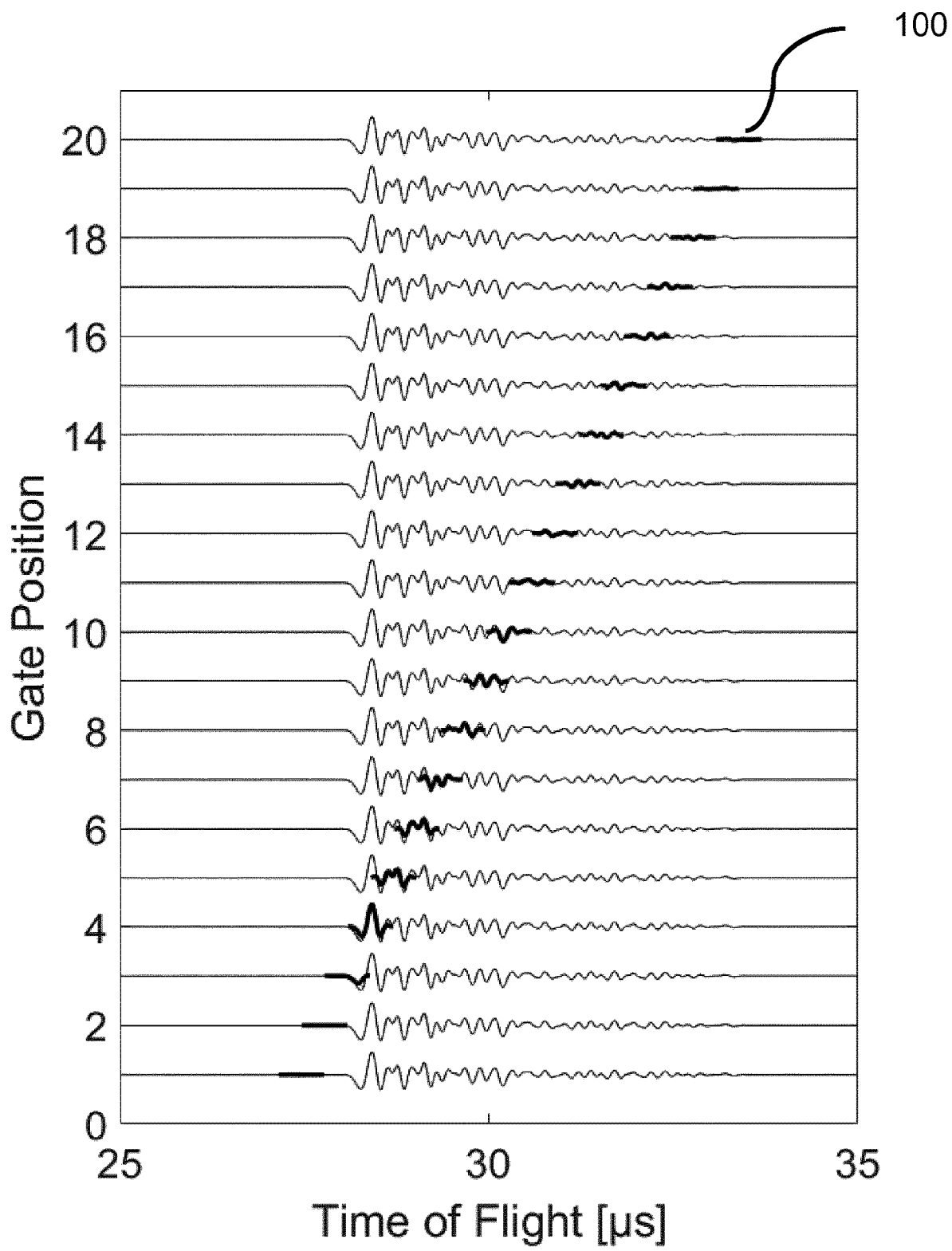
Figure 11:
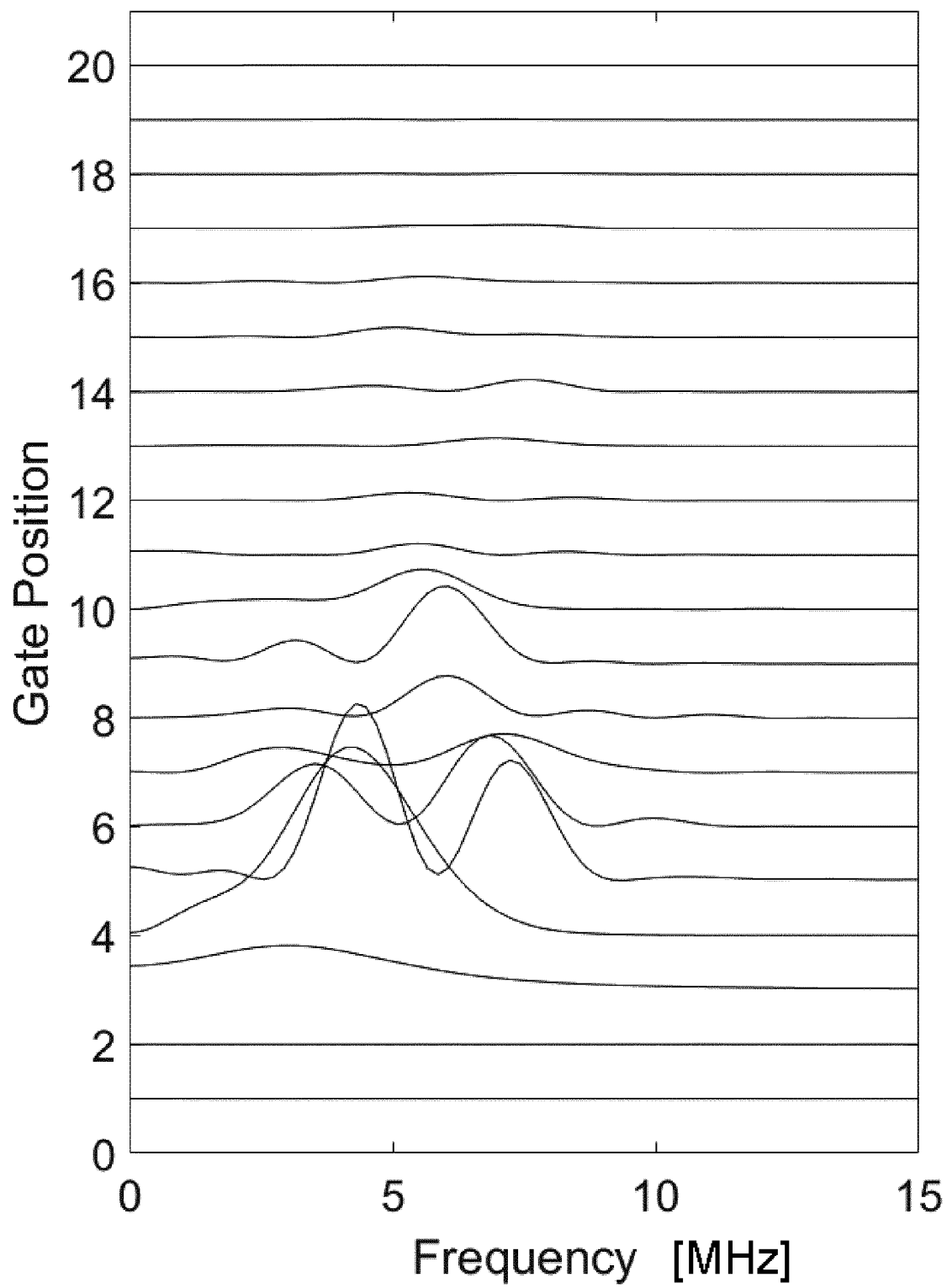
Figure 12:
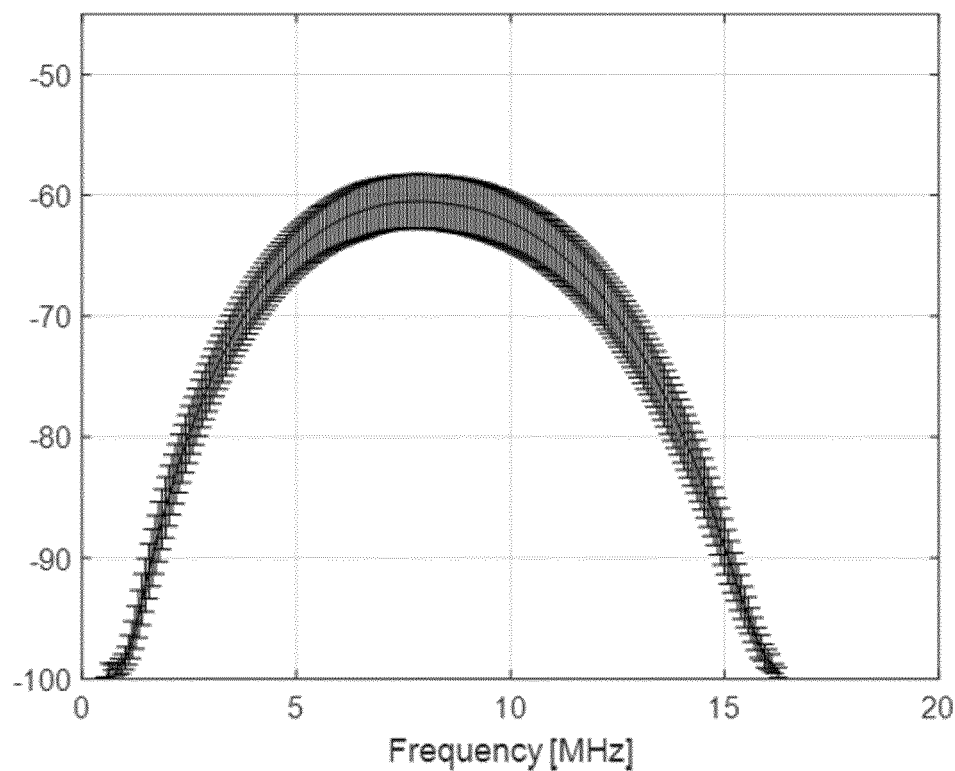
Figure 13:
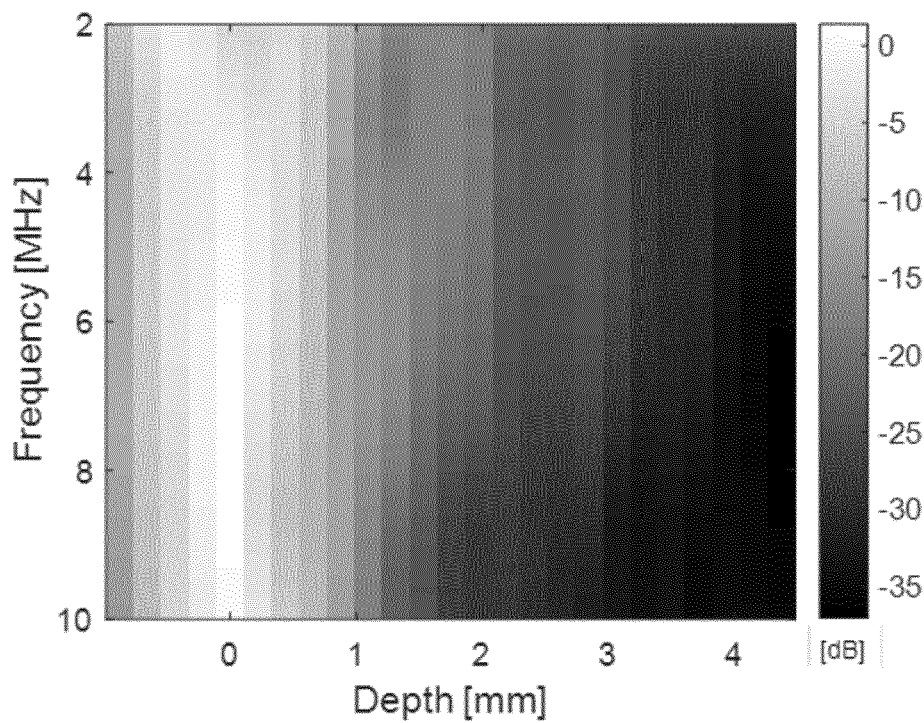
Figure 14:
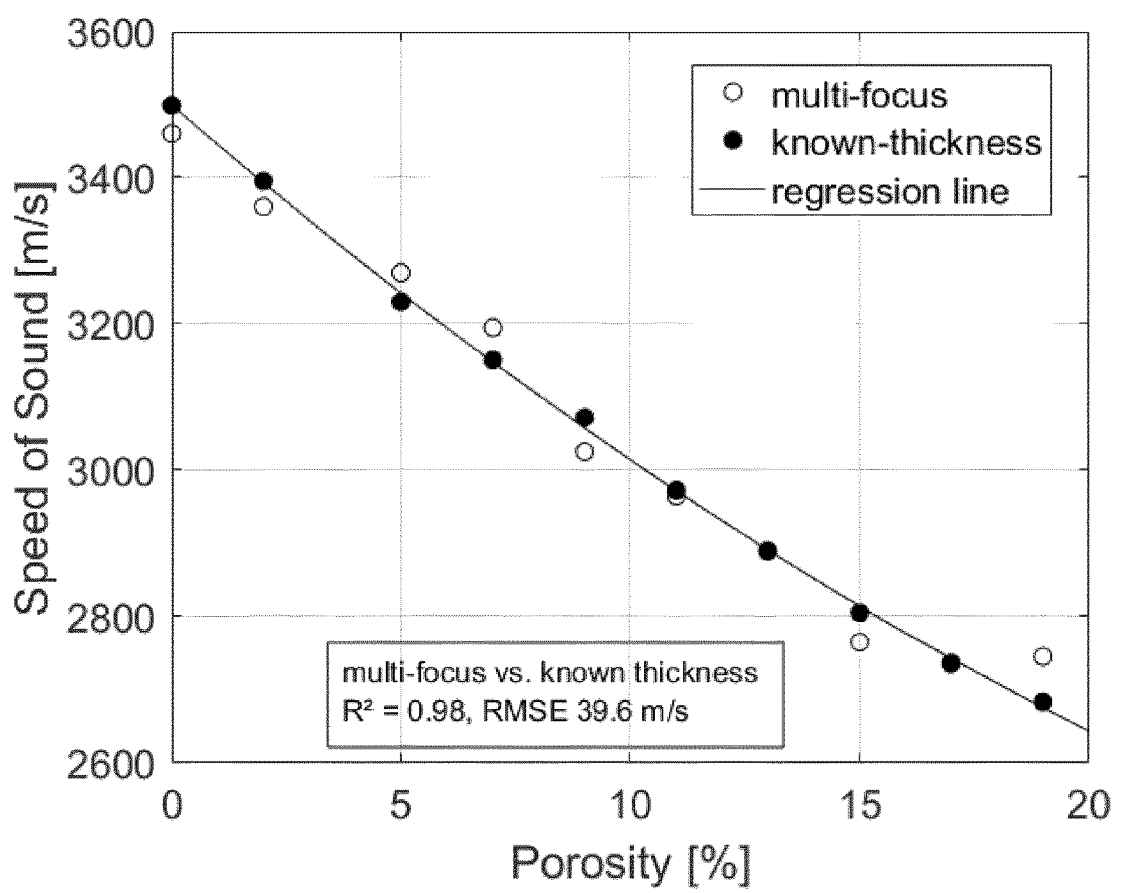
Figure 15:
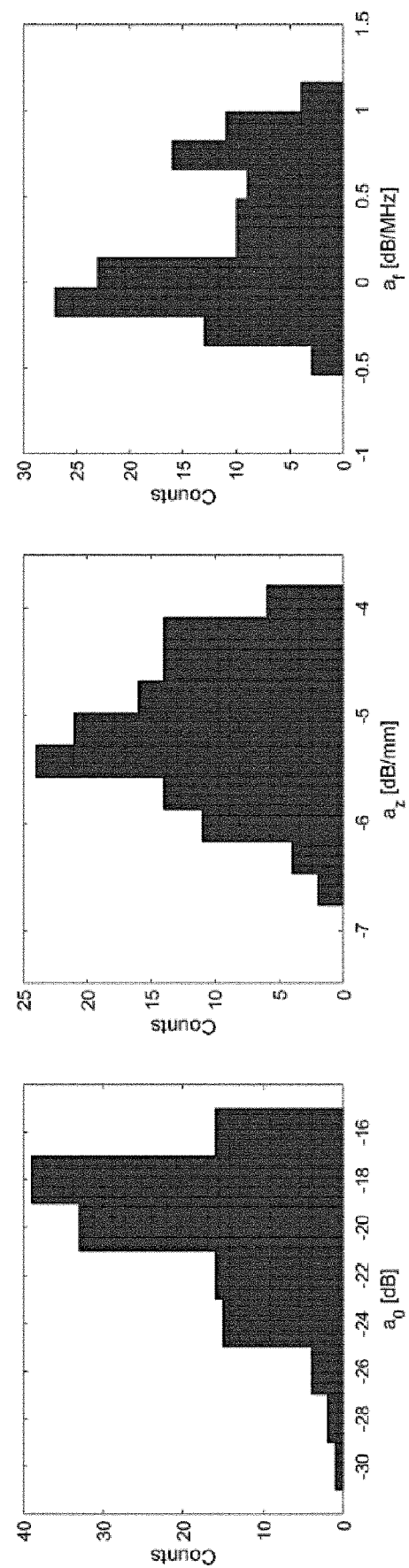
Figure 16A:
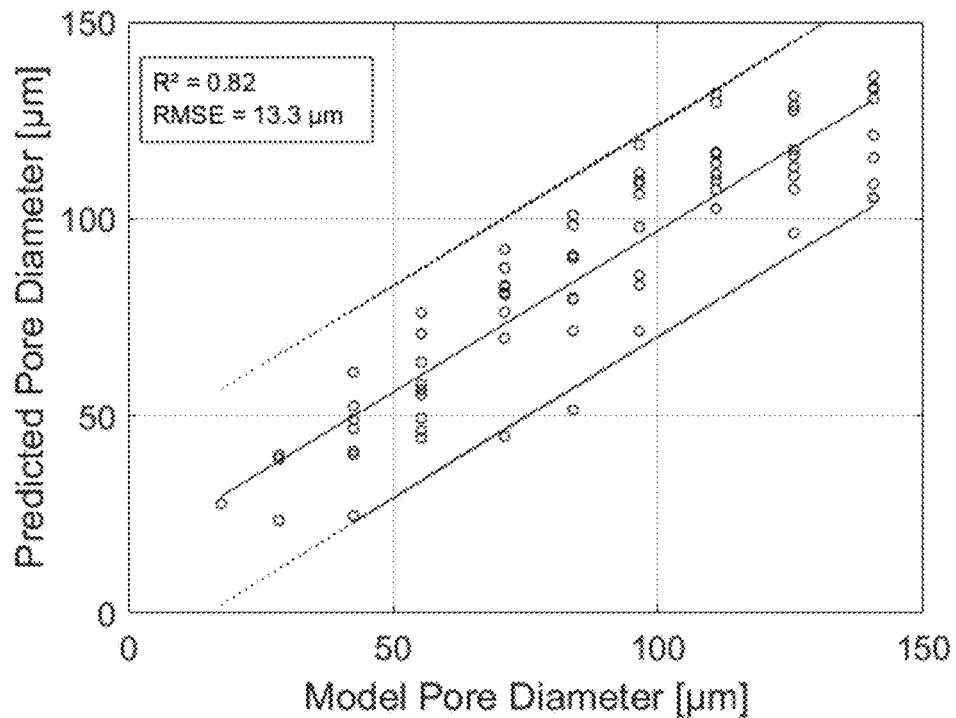
Figure 16B:
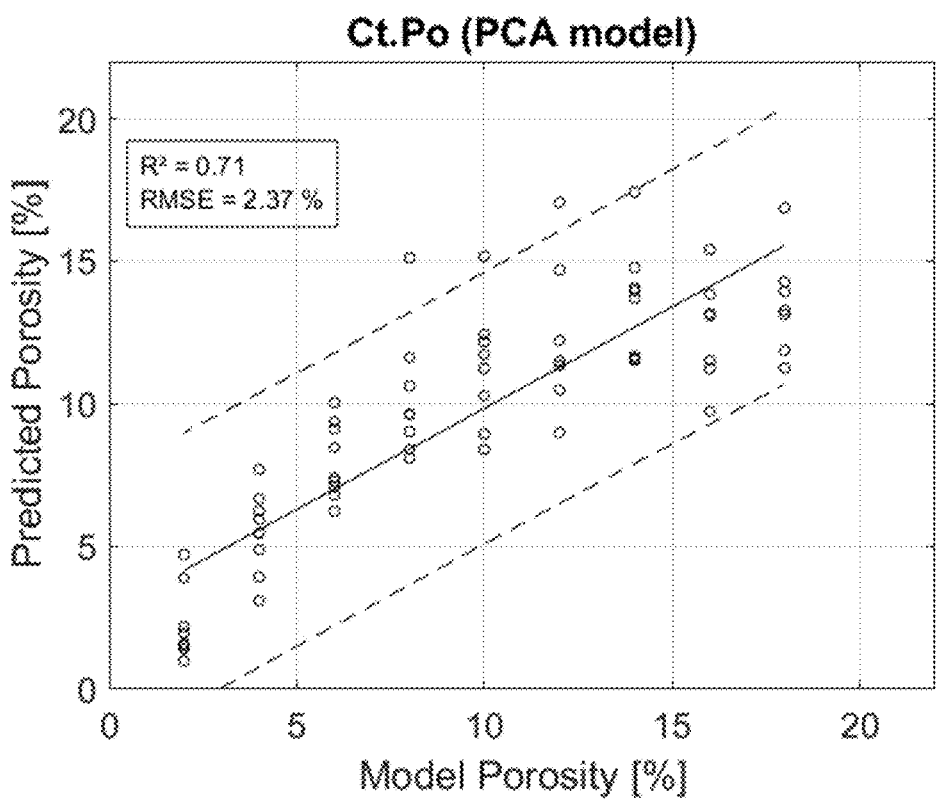
Figure 16C:
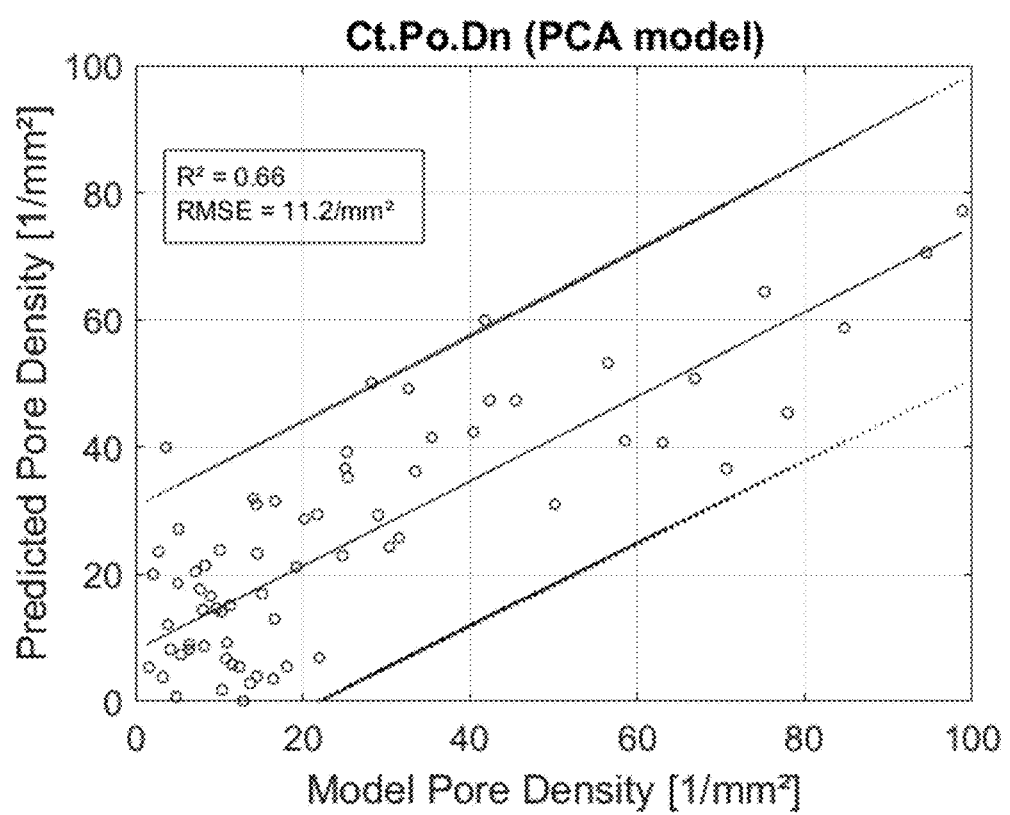
Figure 17:
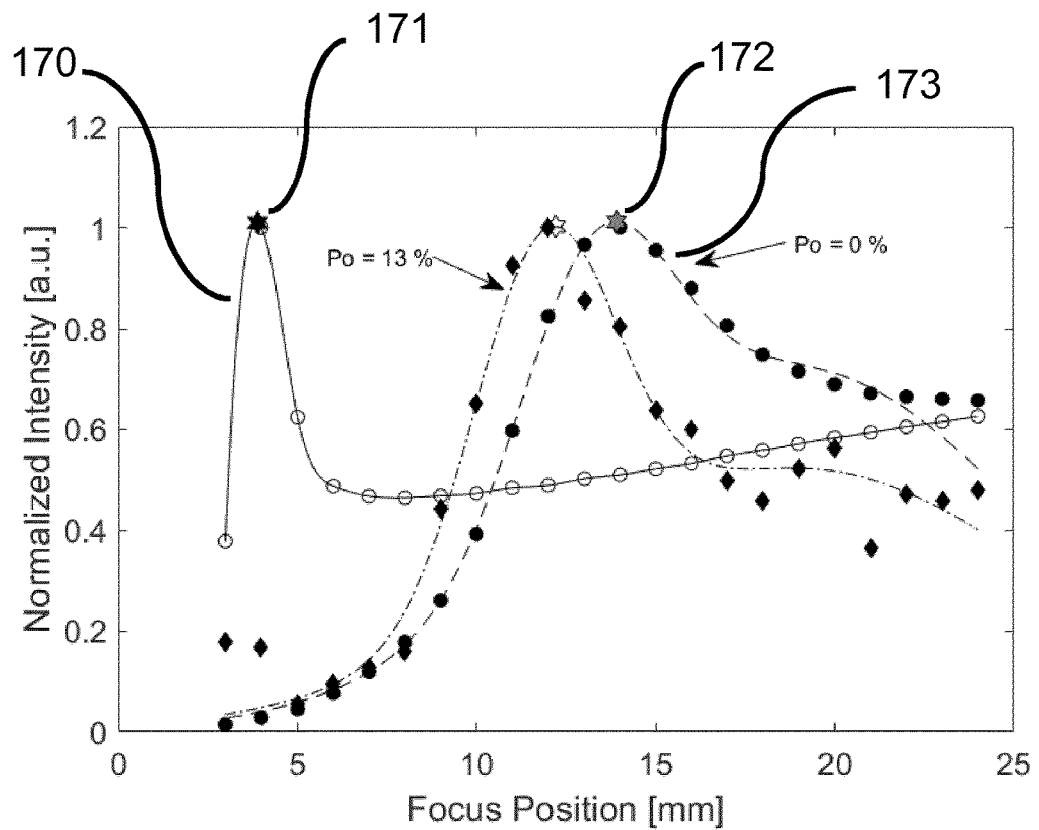
Figure 18:
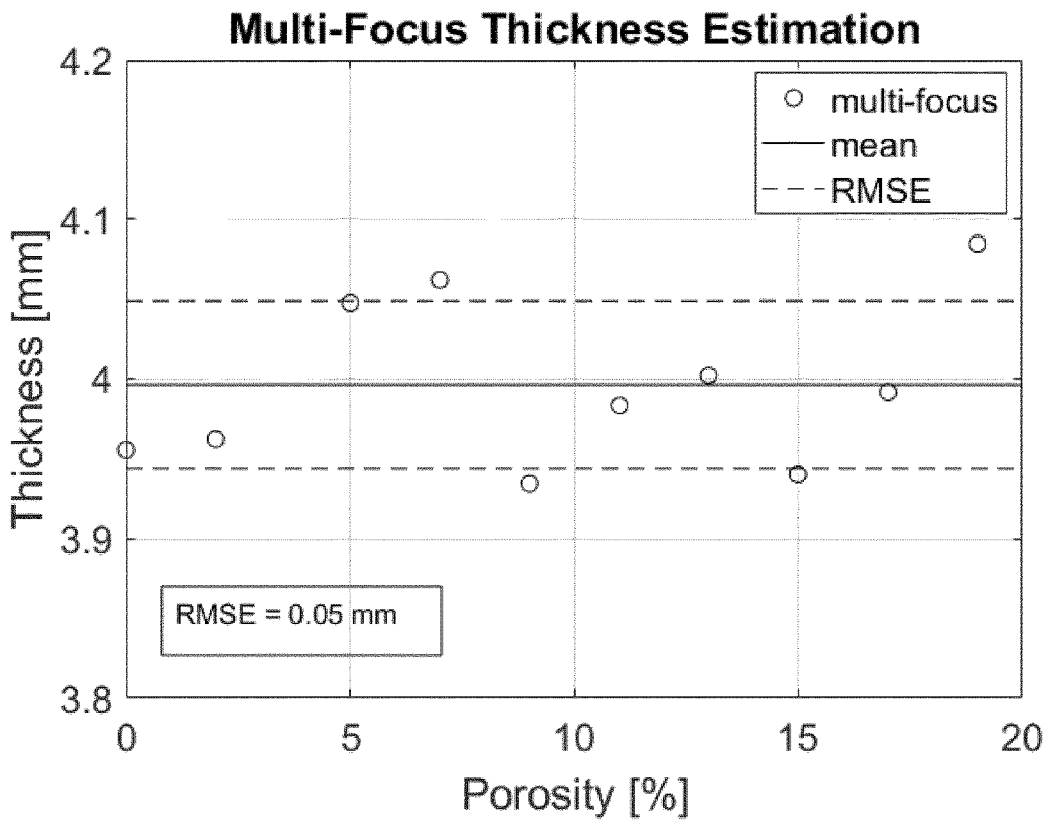
Figure 19:
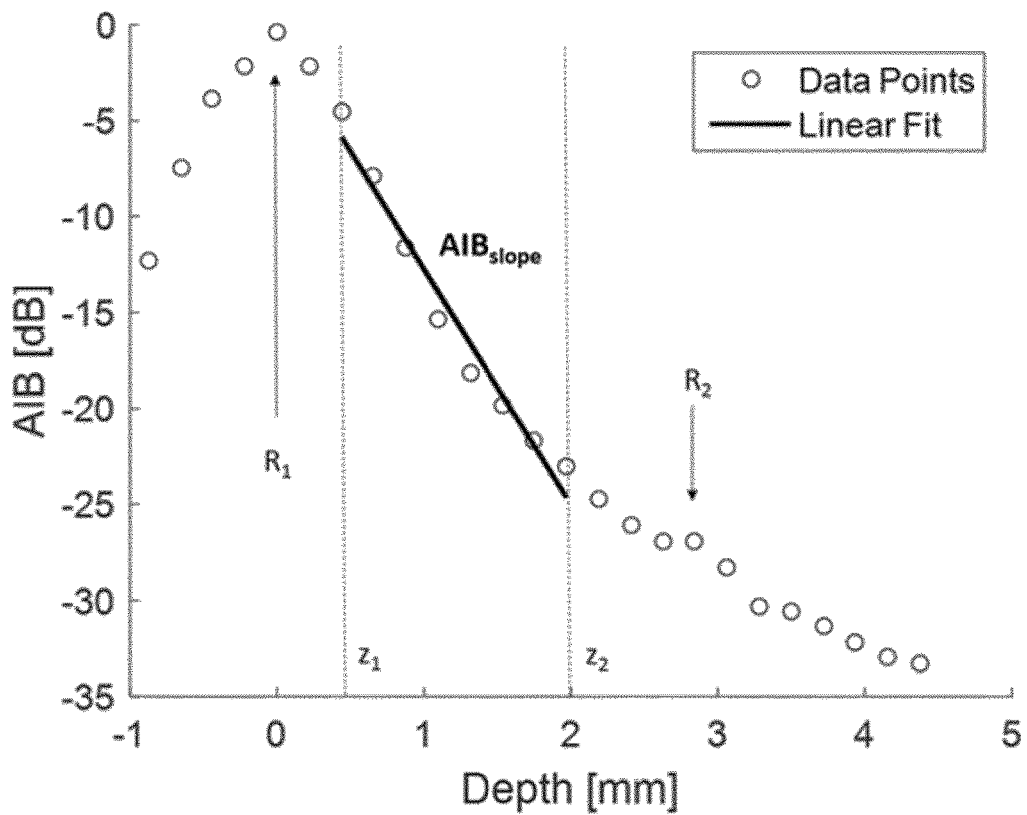
Figure 20:
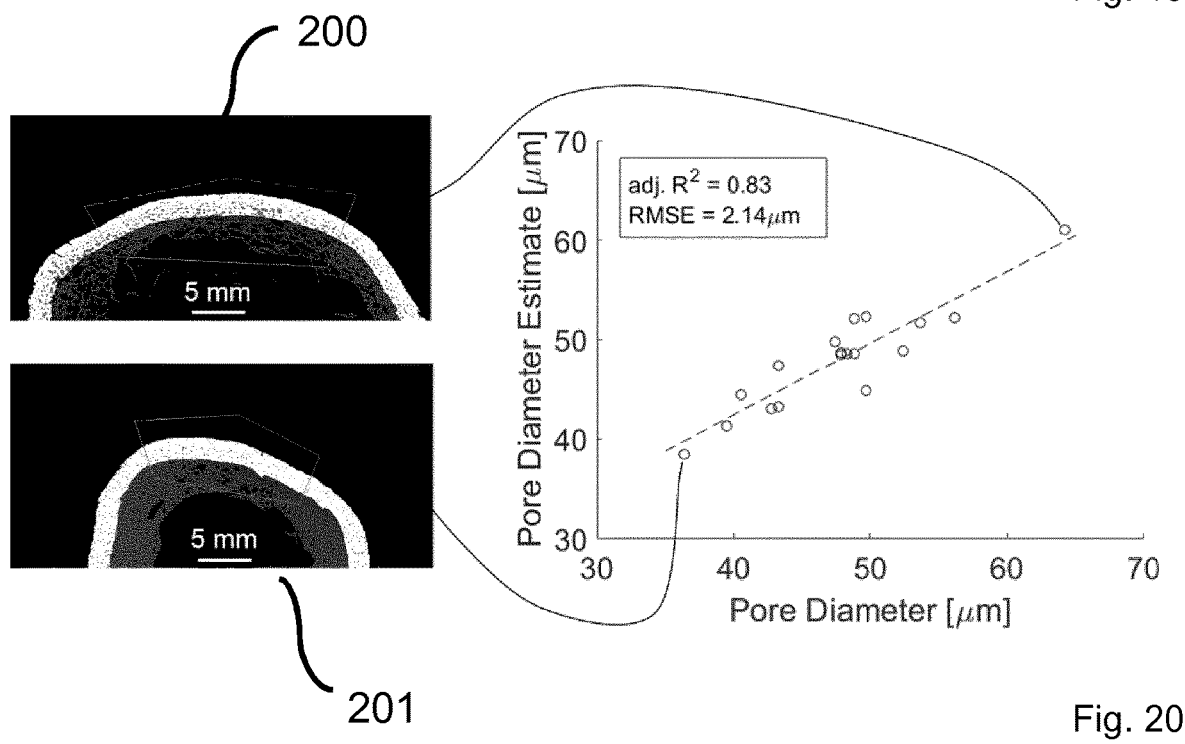
Figure 21:
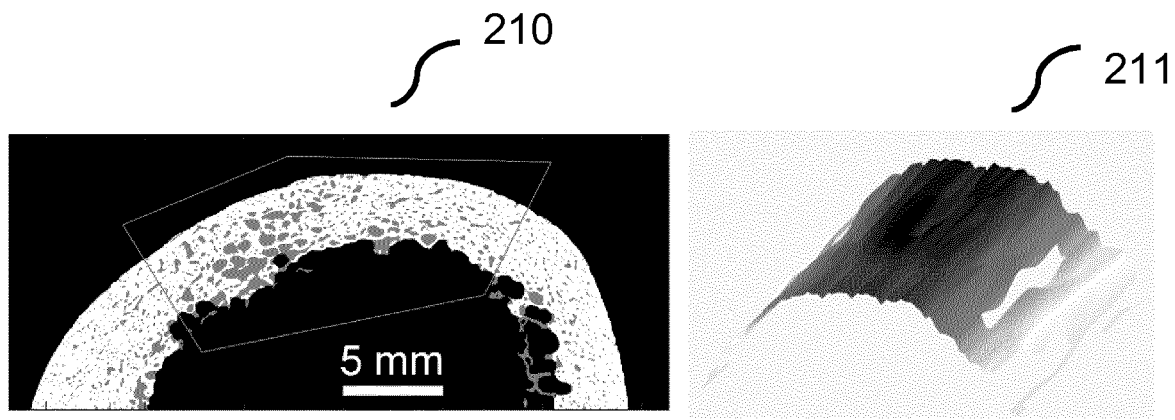
Figure 22:
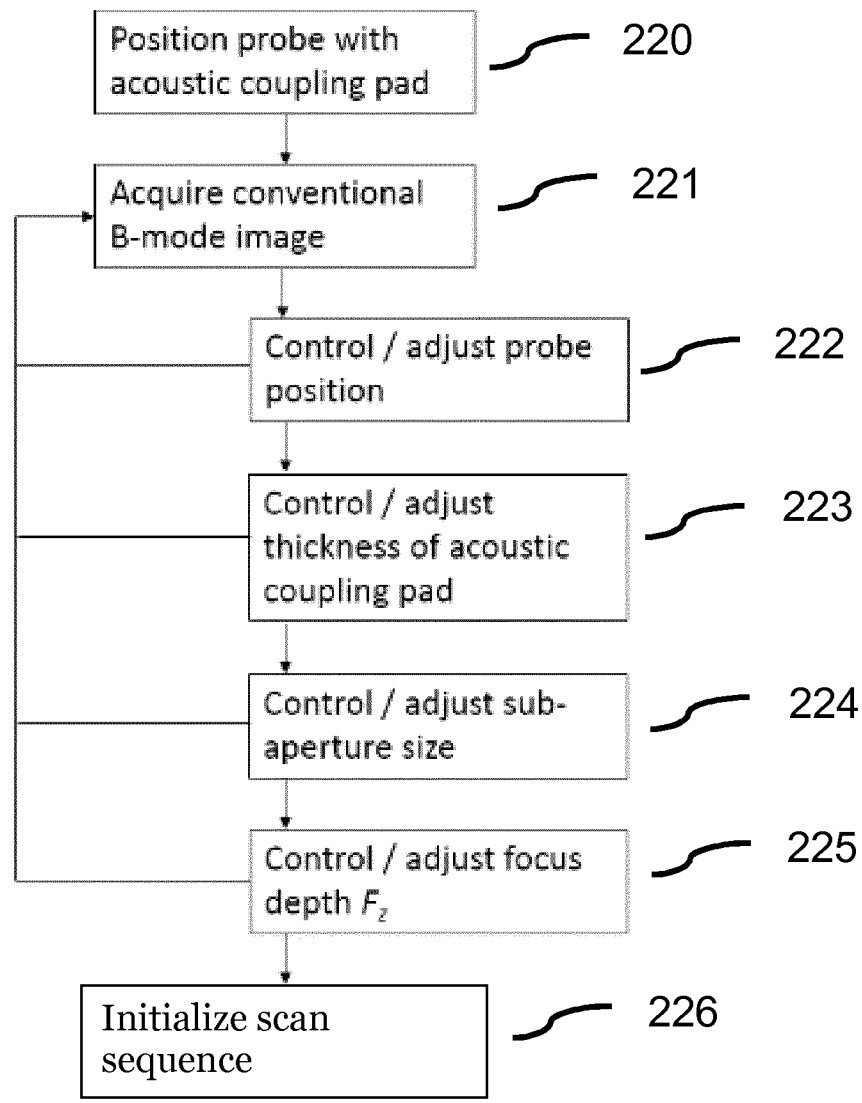
Figure 23:
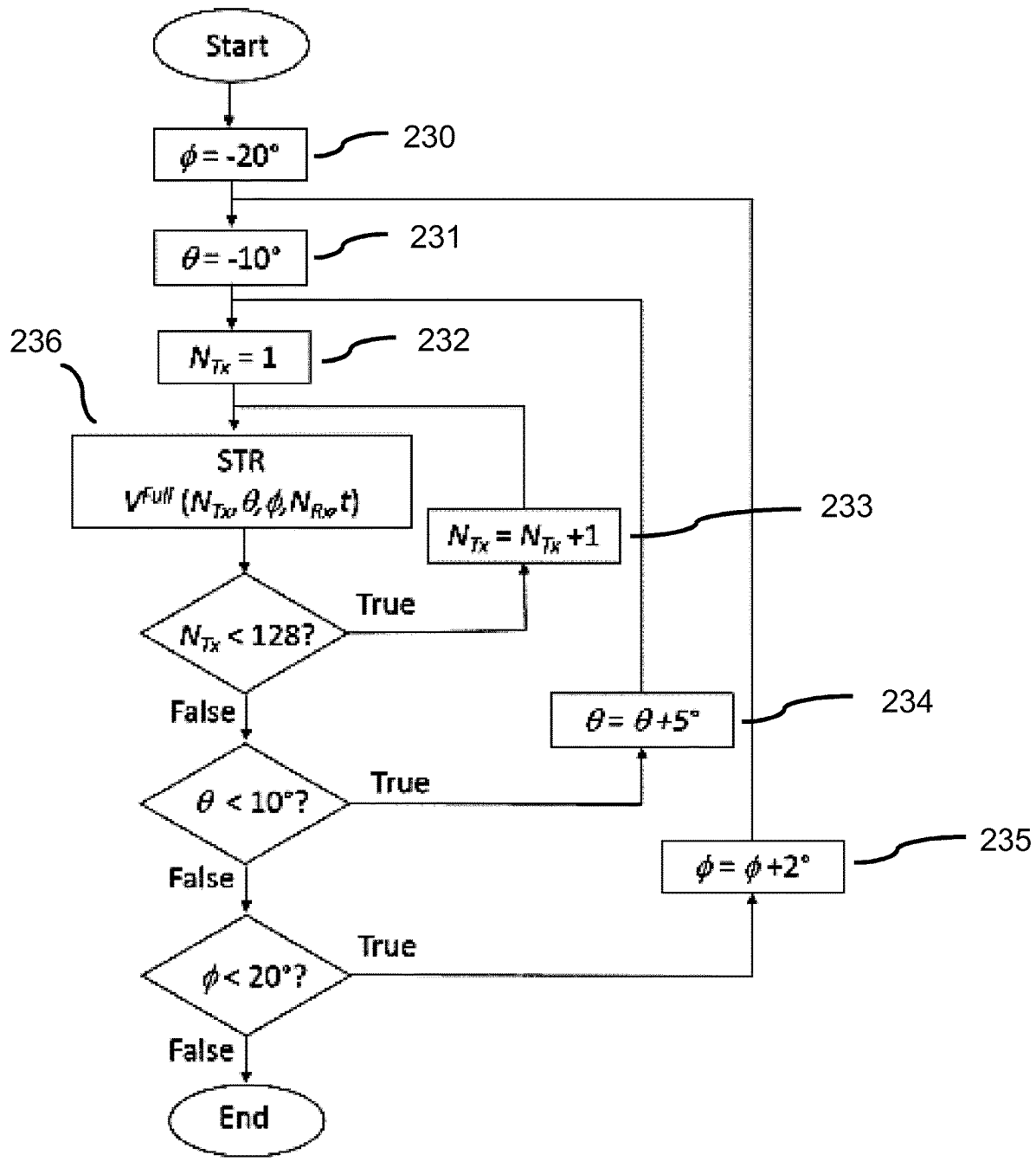
Figure 24:
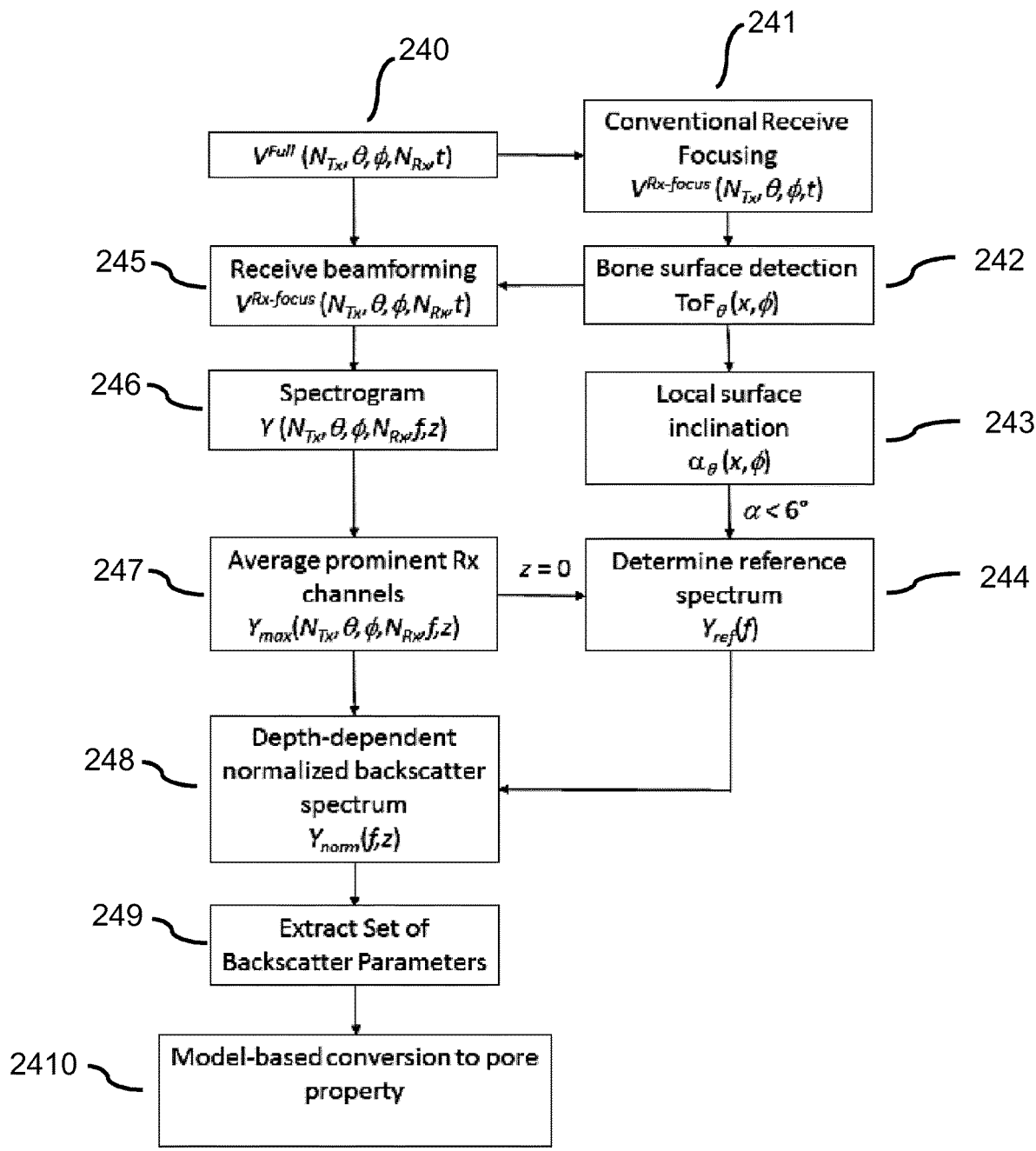
Figure 25:
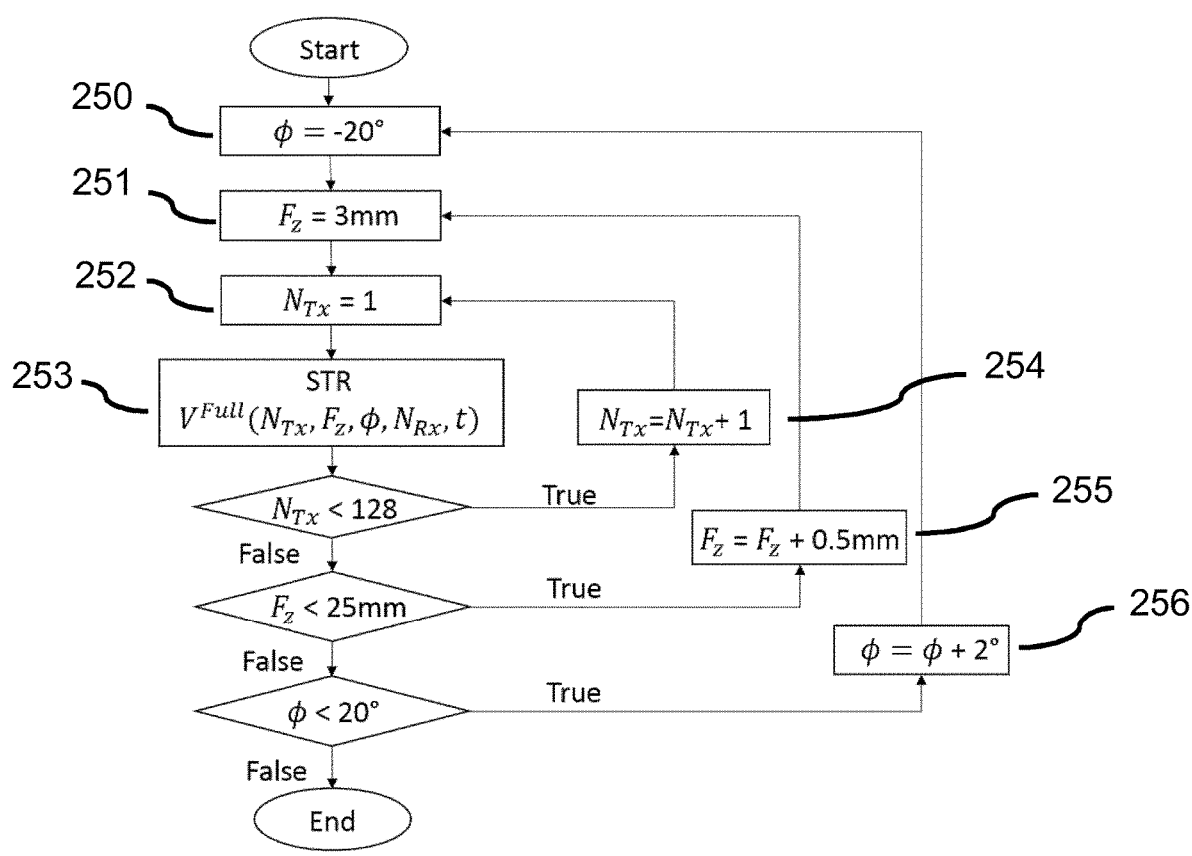
Figure 26:
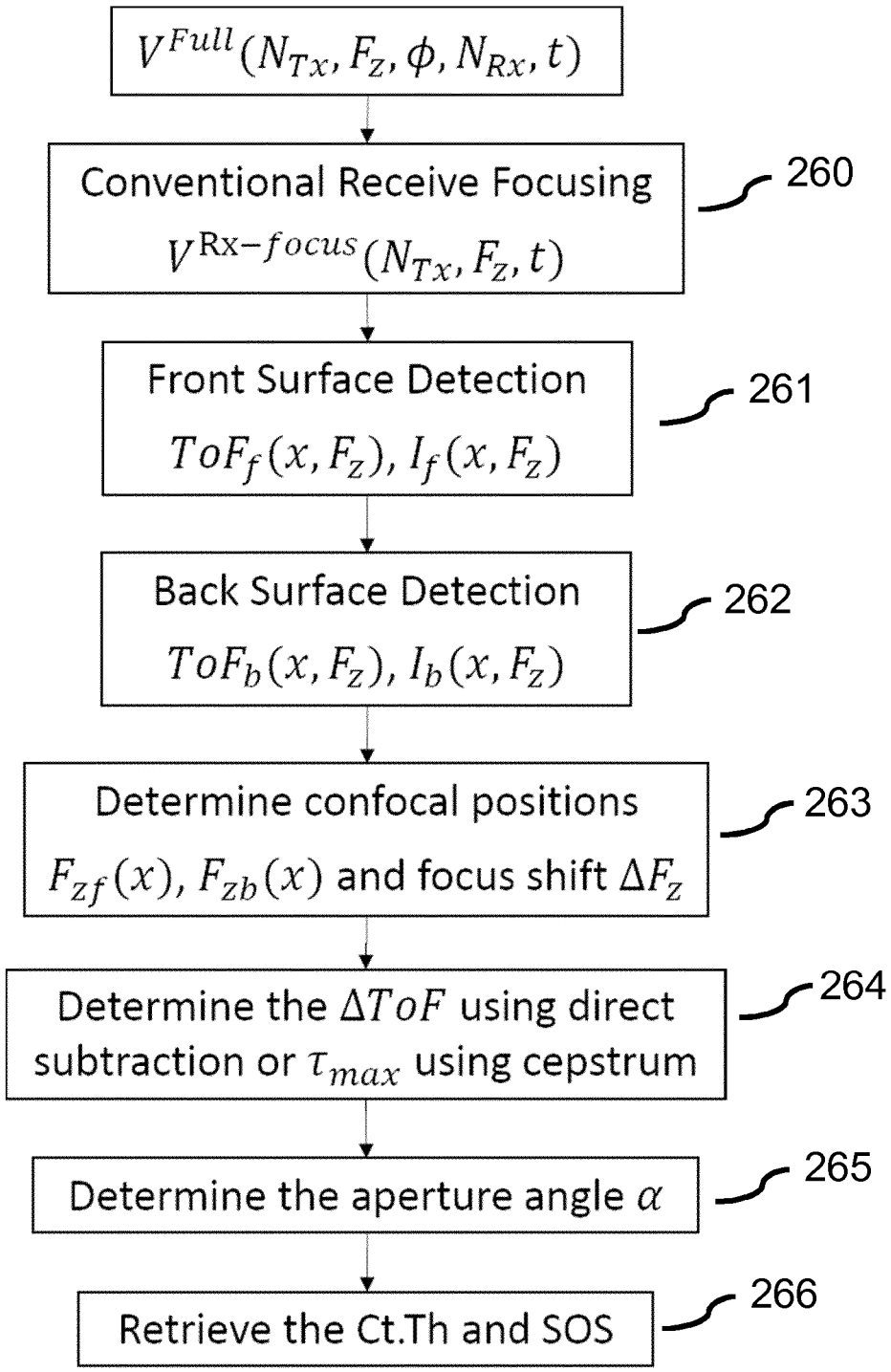
Figure 27:
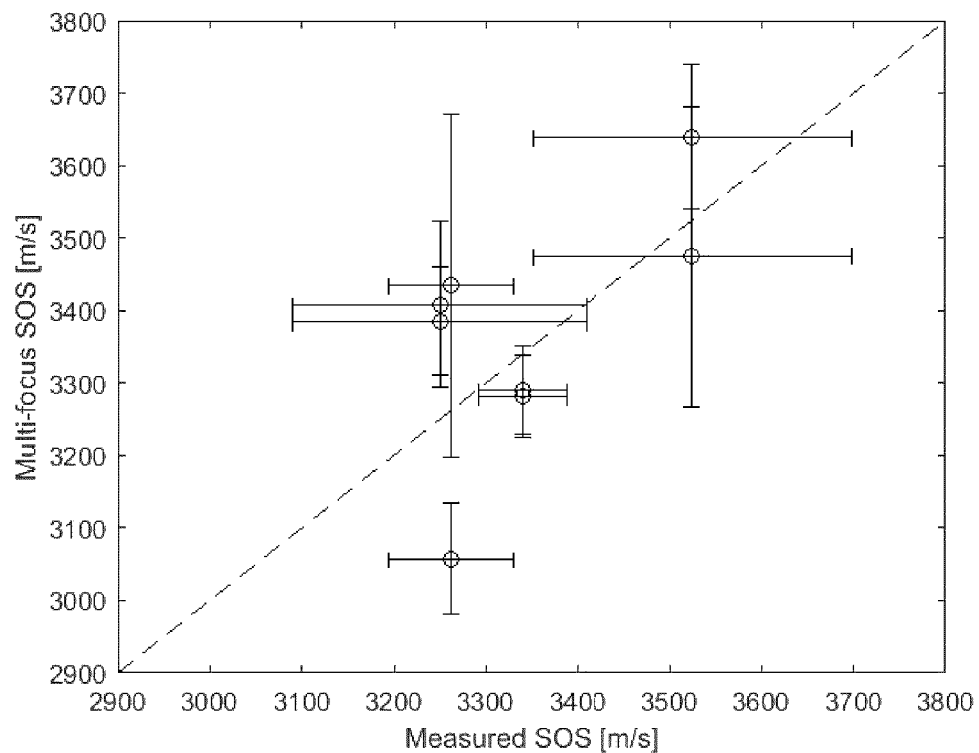
Figure 28:
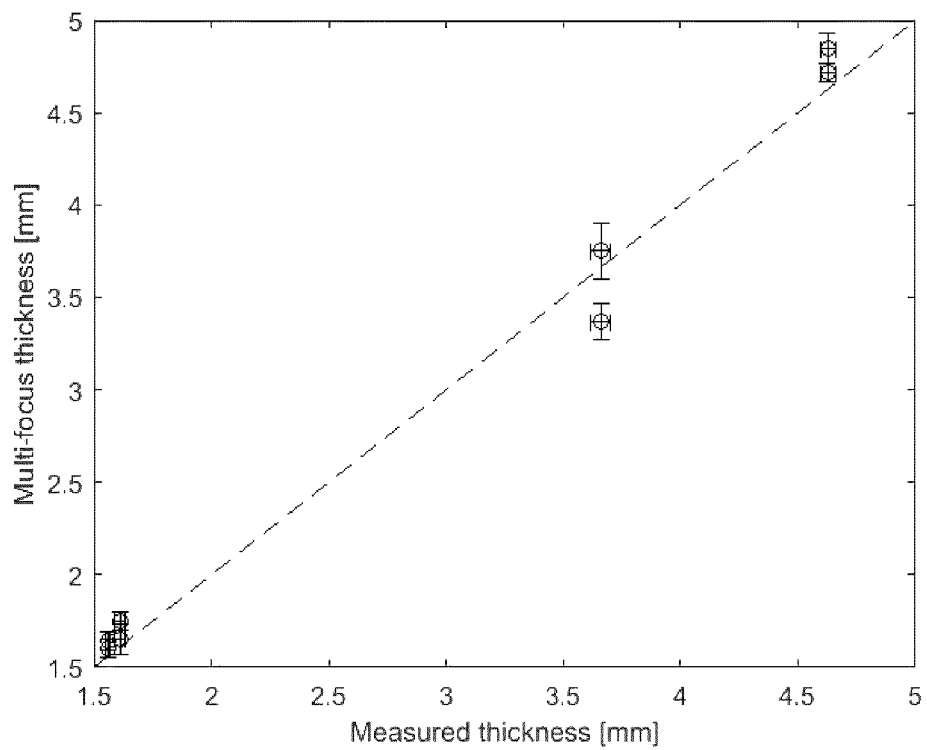

Following, exemplary embodiments are disclosed. The figures show:

FIG. 1 a schematic drawing of one embodiment of the method using a 1D transducer array with transmit focusing, multi-angle beam steering, scan along the transducer array (in x-direction), and sweep scan in the direction perpendicular to the array;

FIG. 2 a schematic drawing of one embodiment of the method using a 1D linear transducer array with transmit focusing, beam steering and scan along the transducer array (in x-direction);

FIG. 3 a schematic drawing of another embodiment of the method using a 1D transducer array with array sweeping (in y-direction);

FIG. 4 time-resolved backscatter signals recorded from a Single-Transmit-Receive (STR) sequence;

FIG. 5 a backscattering cross-section, which describes the intensity of acoustic backscatter with respect to the product k·a of wave number k and radius a of a scatterer;

FIG. 6 a numerical model of cortical backscatter. The bone model contains pores with a diameter of 80 μm and a porosity of 5%;

FIG. 7 normalized backscatter spectra obtained from a numerical model for fixed porosity (Ct·Po=3%) and variable pore diameters;

FIG. 8 individual B-mode images with the detected surface reflection;

FIG. 9 receive beamforming of the STR sequence shown in FIG. 4; the applied phase shift aligns the echoes arriving from equal depths; and the vertical line corresponds to the time of flight of the bone surface reflection;

FIG. 10 a depth-dependent signal analysis for a single receive channel, wherein small fractions of the receive signals are gated using a Hanning-window (bold portions); the gate is sliding through the signal, starting at 1.5 gate lengths before the time of flight of the bone surface reflection and ending at a time corresponding to the depth of analysis (e.g., 4 mm); and the gate length should be 2.5 times the pulse duration and the gate overlap should be at least 50%;

FIG. 11 a depth-dependent spectral analysis of time-gated signals for a single receive channel;

FIG. 12 a representative reference spectrum obtained from STRs with small beam inclination and gating of the specular surface reflection;

FIG. 13 a representative normalized depth-dependent normalized backscatter spectrum obtained from STRs with small beam inclination and averaging spectra for distinct gate positions;

FIG. 14 the decrease of the speed of sound (for fixed tissue matrix properties: transverse elastic coefficient $c_{11}$=23.7 GPa, mass density p=1.93 g/cm$^3$) with increasing porosity obtained from numerical simulations. The filled dots are calculated with a known cortical bone thickness of 4 mm. The hollow dots are calculated using the multi-focus approach;

FIG. 15 the range of parameters $a_0$, $a_z$, $a_f$, of the normalized backscatter spectrum obtained from a parametric numerical simulation study;

FIG. 16 the correlation between model of pore diameter (FIG. 16A), porosity (FIG. 16B), and pore density (FIG. 16C) and their corresponding values predicted from the backscatter parameters;

FIG. 17 a representative result of the tracking of front (solid line) and back-side reflections (--: 0% porosity; -.-: 13% porosity) using the multi-focus approach; the stars indicate the estimated confocal positions; and for illustration purposes the individual lines have been normalized to the respective confocal intensities;

FIG. 18 the accuracy of the thickness estimation (for a fixed thickness of 4 mm) for various porosities using the multi-focus approach;

FIG. 19 a representative depth-dependent AIB: $R_1$ at z=0 mm corresponds to the specular reflection from the outer bone surface. The value after normalization is 0 dB; at a distance of z~2.9 mm a second small peak $R_2$ is visible, which corresponds to the reflection from the inner bone interface; between these two peaks, a smooth decrease of AIB arises from signals backscattered from internal pores; the depth-dependent slope (AIBslope) is obtained by linear regression in a region between these peaks, e.g. between 0.5 and 2 mm;

FIG. 20 Left: Segmented acoustic microscopy images show two samples with extreme differences in the median pore diameter (only a 2 mm stripe below the outer bone surface was evaluated), and Right: An excellent correlation between real and predicted pore diameter was obtained by site-matched evaluation of the present method and SAM data and non-linear multivariate regression analysis;

FIG. 21 Left: Segmented acoustic microscopy image shows a cross section of a human proximal femur shaft (cortical pores are shown in grey), and Right: A 3D reconstruction of the outer surface contour of the same region measured by the present method, where the gray value represents the surface inclination;

FIG. 22 a flow chart for measurement preparation;

FIG. 23 a flow chart for multi-angle scanning;

FIG. 24 a flow chart for data processing;

FIG. 25 a flow chart for multi-focus scanning;

FIG. 26 a flow chart for multi-focus data processing;

FIG. 27 a graphical representation for multi-focus speed of sound (SOS) in dependence on measured SOS and FIG. 28 a graphical representation for multi-focus bone thickness in dependence on measured thickness.

FIG. 1 shows a schematic drawing of an ultrasonic measurement at a bone 1. A sensor 2 comprises an array of ultrasound transducer units 3. Arrow 4 refers to a multi-focus and multi-angle beam inclination with respect to the array normal direction. Arrow 5 refers to a multi-angle sweep of the array perpendicular to the array direction. Arrow 6 relates to a beam scan along the array direction. For each transmitted pulse, the received signals on all channels (here 128 channels) are recorded individually. The time for the acquisition is approximately 2 seconds.

Bone assessment using ultrasound is divided into methods targeting cancellous bone and cortical bone. Most established US techniques target cancellous bone. The present disclosure measures the speed of sound, thickness, and microstructural features in cortical bone.

In one embodiment, the present disclosure evaluates high-frequency waves scattered at the cortical pore network. The small dimensions of the cortical shell relative to the acoustic wavelength render the analysis of backscattered signals from cortical tissue challenging. The present method may employ multidirectional (3D) emission and reception of high-frequency waves using a programmable medical ultrasound scanner and single-channel spectral backscatter analyses to directly assess cortical pore size, pore density, and porosity.

In one embodiment, the present disclosure evaluates high-frequency waves reflected at front and back sides of the cortical bone. The pulse travel time delay between these waves depends on the numerical aperture and on thickness and speed of sound of the bone material. The latter depends on the tissue matrix stiffness in the propagation direction and on the porosity of the material. The present method may employ multidirectional (3D) and multi-focus emission and reception of high-frequency waves using a programmable medical ultrasound scanner and cepstral signal analysis to directly assess cortical bone thickness and speed of sound of cortical bone.

In one embodiment, the method has been developed and validated ex-vivo using a commercial medical ultrasound scanner (i.e., Ultrasonix Touch Research) equipped with a 3D linear transducer array (i.e., 4DL14-5/38). The scanner has a research interface and a DAQ data acquisition box, which provides full control of all hardware parameters and access raw data for all 128 channels. For the measurement, the transducer is positioned on the skin using a gel pad. Special beam-steering sequences have been developed to send focused beams at multiple inclination angles to the cortical bone surface. The sweep motor of the probe allows scanning a 3D volume. For each transmit beam, the full aperture is used to obtain a wide-angle phase-sensitive detection of backscattered signals.

The method provides the acquisition and spectral analysis of reflected and backscattered waves with full control of the transmit beam inclination relative to the outer bone surface. This is achieved by means of a multidirectional multi-focus transmit sequence in combination with a phase-sensitive wide-angle and time-resolved reception of the backscattered signals. In particular, a multi-element (e.g., N=128 elements) linear array (FIG. 2) mounted to a mechanical stage that allows an oscillating sweep motion of the array in the direction perpendicular to the array long axis within a certain sweep angle range (e.g., $\phi=\pm15°$) in a sealed housing (FIG. 3) is used. The array comprises multiple ultrasound transducer units 10 (also called sub-apertures). Alternately, a 2D transducer array can be used (not shown). The proper coupling of the transducer surface array to the object is ensured by a flexible acoustic gel pad 11 and acoustic coupling gel. The object comprises soft tissue 12, cortical bone 13, and bone marrow 14. The array emits focused ultrasound waves which backscatter at the cortical bone 13 leading to backscattered waves 15 and specular reflections 16.

Several sequences for transmitting ultrasonic waves are provided which are further described in the following.

Single transmit-receive (STR) sequence 236: A focused ultrasound beam is generated using compound beam steering technology, i.e., transmit frequency, sub-aperture size, position, direction, and focus distance of the transmit beam are controlled by activating a sub-aperture 10 of the array.

Wide-angle phase-sensitive (WAPS) detection: In contrast to conventional compound B-mode (Brightness mode) imaging 81, in which a sub-aperture centered around the same sub-aperture as for the transmit beam is used for receive beamforming, backscattered waves are collected individually from each array element of the full array (FIG. 4). This is achieved either by simultaneous collection of receive signals from all elements, or by repeated firing of one sub-aperture and subsequent switching of the active receive element from 1 to N. The latter method can be implemented in conventional ultrasound scanner systems without the need of additional acquisition hardware.

A thickness of an acoustic coupling pad 11, a sub-aperture size n and a focus depth $F_z$ 17 are selected such that a focus zone of the transmitted acoustic beam is coinciding with the object of interest. The individual steps for the preparation of the measurement sequence are shown in FIG. 22. The probe is coupled to the body using an acoustic gel pad 220. The proper probe positioning and selection of the region of interest 222, thickness of the coupling pad 223, and setup of scan parameters, i.e., sub-aperture size 224 and focus depth 225 is guided by means of conventional ultrasound B-mode imaging 221. After adjustment and image-guide hardware parameter adjustments, the measurement scan sequence is initialized 226.

For a single transmit event, N time-resolved high-frequency receive signals are recorded with a sampling rate sufficient to fulfill the Nyquist theorem, e.g., >20 MHz (FIG. 4). The result is a 2D matrix of voltage values of the form $$V^{STR}(N_{Rx},t), \qquad (1)$$

whereas $N_{Rx}$ and t are receive channel number and sampling time points, respectively.

Multi-angle Scanning: The STR sequence is repeated until the object has been probed in the desired volume of interest from a sufficiently large range of directions.

The following parameters may be varied (see FIG. 23):
Multiple sub-aperture positions 232 for scan in x-direction, e.g., $N_{Tx} \in [1, \ldots, 128]$ 233,
Multiple transmit beam directions 231, e.g., $\theta \in [-10°, -5°, 0°, 5, 10°]$ 234, and/or
Multiple sweep angles 230, e.g., $\phi \in [-20°, -18°, \ldots, 20°]$ 235.

The result is a 5D matrix $V^{Full}$ 236 of the form $$V^{Full}(N_{Tx},\theta,\phi,N_{Rx},t). \qquad (2)$$

A flow chart for the acquisition of a full multi-angle scan sequence is shown in FIG. 23.

Multi-focus Scanning: The STR sequence is repeated until the object has been probed in the desired volume of interest from a sufficiently large range of transmit focus distances. The following parameters may be varied (see FIG. 25):
Multiple sub-aperture positions 252 for scan in x-direction, e.g. $N_{Tx} \in [1, \ldots, 128]$ 254,
Multiple transmit beam focus distances 251, e.g., $F_z \in [3 \text{ mm}, 3.5 \text{ mm}, \ldots, 25 \text{ mm}]$ 255, and/or
Multiple sweep angles 250, e.g., $\phi \in [-20°, -18°, \ldots, 20°]$ 256.

The result is a 5D matrix $V^{Full}$ 253 of the form $$V^{Full}(N_{Tx},Fz,\phi,N_{Rx},t). \qquad (3)$$

A flow chart for the acquisition of a multi-focus scan sequence is shown in FIG. 25. The ultrasound transducer elements emit and receive broad-band, high-frequency ultrasound pulses, e.g., with frequencies f in the range between 1 MHz and 10 MHz. Within this frequency range, fluid filled pores with cross-sectional dimensions much smaller than the wavelength ($\lambda=c/f$, where c is the speed of sound in the solid matrix, e.g., c=3500-4500 m/s for bone) embedded in a solid matrix cause frequency dependent backscatter. If the product of wave number $k=2\pi/\lambda$ and pore radius a is smaller than 1 (Rayleigh scattering), e.g., for pores with a cross-sectional dimension between 10 µm and 70 µm, the backscattering coefficient is approximately linearly increasing (FIG. 5).

For frequencies lower than 1 MHz, the backscatter coefficient diminishes (ka→0) and the axial resolution (which is determined by the wavelength) decreases. While the former increases the ratio between specular reflections and signals backscattered from pores, the latter increases the temporal overlap between reflected and backscattered waves. Both factors aggravate the separation and distinct analysis of reflected and scattered waves. For frequencies larger than 10 MHz (ka>1), the backscatter cross-section does not increase further. Moreover, the attenuation is approximately proportional to $f^2$, which reduces the penetration depth. For ka>1, the sensitivity to changes of the pore dimension becomes more complex due to the oscillatory behavior of the backscatter cross-section with increasing a. Moreover, stronger attenuation due to increasing frequency (and wave number k) aggravates the ability to analyze signals originating from larger tissue depths. Thus, the frequency range between 1 MHz and 10 MHz is ideally suited to separate specular reflections originating from the outer and inner cortical bone boundaries from signals backscattered from internal pores (FIG. 6) and to analyze changes in the backscatter spectrum related to variations of pore dimensions typically found in cortical bone.

Scattering of ultrasound sound waves from multiple fluid-filled pores embedded in a solid matrix is complex and is determined by a plethora of factors, e.g., number, shape, size, and distribution of the scatterers, anisotropic elastic and viscoelastic material properties of the solid matrix, multiple scattering, mode conversions, etc. Acoustic backscatter from trabecular bone has extensively been researched, but the derivation of structure and mechanical properties remain difficult due to the complex and irregular structure of the trabecular network. So far, no comprehensive theory incorporation all influencing factors exists. Finite-difference time-domain analysis represents a powerful numerical tool for studying the sound propagation in complex media. The inventors have shown previously that the frequency dependence of cortical backscatter is strongly related to the size distribution of cortical pores. Pores of increasing size result in a characteristic alteration of the normalized backscatter spectrum (FIG. 7). The response is similar to a low-pass filter, whereas the pore dimension is associated to the cut-off frequency.

The data analysis may comprise i) detecting the outer bone surface from the receive-beamformed 3D volume (FIG. 8), ii) determining a reference spectrum from surface reflections measured at normal incidence (e.g., autocalibration to compensate for attenuation losses in the soft tissue) (FIG. 12), iii) calculating a depth-dependent normalized backscatter spectrum (FIG. 13) and extracting representative parameters, e.g., a depth- and frequency dependent slope and intercept values of the normalized backscatter spectrum (FIG. 15), and other characteristic features of the normalized backscatter spectrum, e.g., the apparent integrated backscatter intensity, iv) determining confocal positions and travel time delay of front and back-side reflections for each scan position (FIG. 17), and determining speed of sound and thickness of the bone using ultrasound refraction-based relationships The steps are further described in the following.

A flow chart for the backscatter analysis is shown in FIG. 24.

i) Bone Surface Detection

Conventional receive beam steering technology 241 is applied to the collected data set 240 to reconstruct B-Mode images 80 for each sweep angle ϕ, i.e., receive focusing, apodization, summation, envelope detection, and spatial compounding are applied to the collected data 81. Conventional threshold and edge detection algorithms 242 are applied to detect the time of flight of the outer bone surface $ToF_\theta(x,\phi,\theta)$ 80 and after appropriate scaling, local surface inclination maps $\alpha_\theta(x,\phi,\theta)$ 211 for each transmit beam steering angle θ are obtained 243 (FIG. 21).

ii) Determination of the Reference Spectrum Using a Sliding Window Spectral Analysis First, receive beamforming 245 is applied to each STR sequence (FIG. 9) to align the signals reflected from the outer bone surface to a common pulse travel time 90.

Then, a spectrogram 246 is calculated from each receive channel by extracting a gated signal 100 from various depths z relative to the bone surface (i.e., z=0), e.g., using a sliding Hanning gate (FIG. 10). From each gated window, a power spectrum (FIG. 11) is calculated, e.g., using the Fast Fourier Transform (FFT). The result is a 6D matrix of the form $$Y(N_{Tx},\theta,\phi,N_{Rx},f,z). \tag{4}$$

For each STR, the channels with prominent spectral intensity (e.g., >−5 dB relative to maximum) are grouped and averaged 247. The result is a 5D matrix of the form $$\max[Y(N_{Tx},\theta,\phi,N_{Rx},f,z)]=Y_{max}(N_{Tx},\theta,\phi,f,z). \tag{5}$$

From these spectra, those which were measured with approximately normal incidence (e.g., an inclination of α<6°) 243 and z=0 (surface reflection) 242 are averaged (FIG. 12). Alternatively, an appropriate inclination correction algorithm can be applied to incorporate measurements with inclinations of α>6° in the estimation of the reference spectrum 244. The result is a 1D vector of the form $$\langle Y_{max}(N_{Tx},\theta,\phi,f,z)|_{\alpha<6°,z=0}\rangle=Y_{ref}(f). \tag{6}$$

The reference spectrum represents the total reflected spectral intensity compensated for transmission losses from reflections at interfaces (i.e., transducer-coupling gel, coupling gel—skin, internal soft tissue boundaries) and attenuation on the transmission path. All spectra measured below the bone surface (z<0) contain information from internal cortical bone structures and from the inner cortical bone boundary.

iii) Calculation of a Depth-Dependent Normalized Backscatter Spectrum

The procedure of calculating the average spectrum is repeated for all gate positions z. From each averaged logarithmic spectrum, the reference spectrum is subtracted to obtain the depth-dependent normalized backscatter spectrum 248 (FIG. 13). The result is a 2D matrix of the form $$\langle Y_{max}(N_{Tx},\theta,\phi,f,z)|_{\alpha<6°}\rangle-Y_{ref}(f)=Y_{norm}(f,z). \tag{7}$$

For z<0, the depth-dependence (i.e. the intensity gradient with depth) of the difference spectrum is affected both by the frequency-dependent attenuation and by the frequency dependence of the backscattered signal. A common parameter reflecting these effects is the AIB 249. The result is a 1D vector of the form $$AIB(z) = \frac{1}{\Delta f}\int_{f_1}^{f_2} Y_{norm}(f,z)df \tag{8}$$

wherein $f_1$ and $f_2$ are the integration bounds, which are set such that AIB contains signals within the bandwidth of the transducer and $\Delta f = f_2 - f_1$.

For $z\sim 0$, AIB represents the specular reflection intensity. If the gate position is equal to the two-way travel time to the back-side bone surface, the signal reflected at this interfaces contributes to the measured AIB. Between these gate positions, AIB is associated with signals backscattered from internal pores (FIG. 19). The slope of AIB with respect to depth (AIB$_{slope}$=$\delta$AIB/$\delta$z) can be extracted, e.g., in a depth-range from 0.5 mm to 2 mm. The result of this procedure is a single parameter. By the integrating over all frequencies detailed information about the frequency dependence is lost. This information can be kept by fitting a plane to $Y_{norm}(f, z)$ within a specific frequency range, e.g., 3 MHz to 7 MHz. With this plane-fit approach, the normalized backscatter spectrum is modeled by a set of four parameters 249:

$$Y_{norm}(f,z) = a_0 + a_z z + a_f f. \quad (9)$$

iv) Calculation of Speed of Sound and Thickness

In order to retrieve both the cortical thickness and the speed of sound independently, a multi-focus technique can be applied. A flow chart for the multi-focus analysis is shown in FIG. 26.

Transmit and receive focus are successively varied and for each focus position, pulse travel times and amplitudes of the reflections of front 170 and back side 173 echoes are tracked (FIG. 17).

Conventional receive beam steering technology 260 is applied to the collected data set to reconstruct B-Mode images 80 for each transmit focus $F_z$ and $\phi$, i.e., receive focusing, apodization, and summation are applied to the collected data. The detection of the outer bone surface is similar to the procedure described in i).

Moreover, for each scan position x and transmit focus $F_z$, pulse travel time ToF$_f$ and intensity $I_f$ of the reflected signals are stored 261. Similar procedures are applied to detect the back-side reflections and their corresponding pulse travel time ToF$_b$ and intensity $I_b$ 262.

From this data the front and back-side focus positions $F_{zf}$ and $F_{zb}$, respectively, and the necessary focus shift $\Delta F_z$ can be determined 263. A focus shift $\Delta F_z$ needed to maximize the signal of either front 171 or back side 172 reflections is determined by Ct·Th, by the speed of sound in soft tissue $c_0$ and bone $c_p$, and by an aperture angle $\alpha$ of transmit and receive beams.

$$Ct.Th = \frac{\Delta Fz}{\frac{1c_p}{2c_0}\left(1 - \frac{c_p^2}{c_0^2}\right) \cdot (1 - \cos(k_{app}\alpha)) - \frac{c_p}{c_0}}. \quad (10)$$

For the calculation of the pulse echo travel time delay $\Delta$ToF 264 either conventional echo tracking methods or cepstral analysis can be applied. For the earlier, the travel time delay between front and back-side reflections can be obtained by subtracting travel time ToF$_f$ from ToF$_b$. For the latter, a single gate is applied. Start and end positions of the single gate are set equivalent to start and end positions of first and last gates, respectively, of the sliding gate analysis (FIG. 10). The individual spectra are normalized by the reference spectrum $Y_{ref}(f)$, and the cepstrum $C(\tau)$ is calculated by means of a second Fourier transformation within the bandwidth of the transducer and $\Delta f = f_2 - f_1$. All cepstra measured with approximately normal incidence (e.g., an inclination of $\alpha < 6°$) are averaged 265. A peak position $r_{max}$ in the cepstrum $C(\tau)$ is related to cortical thickness Ct·Th and compressional speed of sound $c_p$:

$$\tau_{max} = 2Ct \cdot Th/c_p. \quad (11)$$

In principle, $\tau_{max}$ should be equal to $\Delta$ToF.

By combining Eq. (10) and Eq. (11), Ct·Th and $c_p$ can be determined 266. The coefficient $k_{ap}$ (Eq. 10) is a factor accounting for an apodization reducing the effective aperture angle $\alpha$ 265. The apodization is caused by the gradually increasing conversion of compressional waves into shear waves at the bone interface with increasing beam inclination. The apodization factor depends on the refractive index and the aperture angle used for transmit and receive focusing and should be determined experimentally. The local inclination angle can be obtained similarly to the procedure described in i) and be used to limit the region of interest for thickness and speed of sound estimations.

The associations of backscatter parameters with bone properties 2410 are discussed in the following section.

The method was validated numerically by means of Finite-Difference Time-Domain sound propagation simulations (FIG. 6). Cortical pore diameter Ct·Po·Dm$\in$[28 µm, . . . , 140 µm], pore density Ct·Po·Dn$\in$[1.3 mm$^{-2}$, . . . , 100 mm$^{-2}$], and porosity Ct·Po$\in$[2%, . . . , 18%] were systematically varied. The normalized backscatter model (Eq. 9) could be fitted to all data (0.93≤R2≤0.99). The range of parameters is shown in FIG. 15. While cortical pore diameter Ct·Po·Dm was associated with the frequency and depth dependent variations of the normalized backscatter spectrum, pore density Ct·Po·Dn and porosity were associated with an intercept value $a_0$ and the AIB amplitude:

$$Ct \cdot Po \cdot Dm = 108.6 \text{ µm} - 73.2 \text{ µm MHz/dB } a_f, \quad (12)$$

$R^2 = 0.82$, RMSE=13.3 µm $$Ct \cdot Po = 87\% - 0.61\% \text{ dB}^{-1} a_0 + 2.77 \text{ mm}^{-1}/\text{dB}$$
$$a_z + 2.55\% \text{ dB}^{-1} \text{ AIB}, \quad (13)$$

R2=0.62, RMSE=3.3%

$$Ct \cdot Po \cdot Dn = 139 \text{ mm}^{-2} + 23.7 \text{ mm}^{-1}/\text{dB } a_z + \text{mm}^{-2} \text{ MHz}/$$
$$\text{dB } 44.2 \text{ } a_f, \quad (14)$$

$R^2 = 0.58$, RMSE=15.5 mm$^{-2}$

The prediction models 2410 can be further improved by means of principal components derived from the backscatter parameters and from the AIB.

A correlation between input parameters of the model and the predicted values using Eqs. (12) to (14) is shown in FIGS. 16A, 16B and 16C.

The retrieval of speed of sound and thickness from the multi-focus scan is shown in FIGS. (14) and (18). The method was validated experimentally on a set of 18 human proximal femur shaft samples, for which site-matched parameters describing the pore morphology from low 201 to high 200 pore diameters measured by means of high-resolution acoustic microscopy 210 were available (FIG. 20).

Cortical porosity, median pore diameter, median cross-sectional area, and pore density were obtained within 2-mm stripes below the periosteal (outer) bone surface. An excellent correlation (adj. $R^2 = 0.93$) was obtained with (AIB$_{slope}$). However, the correlation was sensitive to the selected frequency range and required manual adjustment of the evaluation depth. Another robust correlation using a fixed depth range from 0.5 to 2 mm was obtained using the plane-fit approach and multi-variate stepwise regression analysis. The agreement ($R^2=0.83$, RMSE=2.14 µm) between real and predicted pore diameter is shown in FIG. 20.

The retrieval of compressional sound velocity and thickness by multi-focus scanning is discussed in the following section.

The method was validated numerically by means of Finite-Difference Time-Domain sound propagation simulations (FIG. 6). The compressional sound velocity of the bone matrix of a 4-mm plate was set to 3500 m/s. Pore density Ct·Po·Dn∈[1.3 mm$^{-2}$, ..., 100 mm$^{-2}$] was varied using a fixed cortical pore diameter of Ct·Po·Dm=40 μm. The resulting porosity was Ct·Po∈[0%, ..., 19%]. A 2.5 MHz pulse with a bandwidth of 80% was used to model the transmit pulses. 32 array elements were used to scan the transmit focus $F_{Tx}$∈[4 mm$^{-2}$, ..., 25 mm]. The same aperture and focus distance were used for receive focusing. Front and back side echo amplitudes and travel times could be retrieved from all data. The decrease of the compressional bulb wave velocity with increasing porosity was determined from the pulse travel time difference and the known thickness using Eq. (10). The estimation of the speed of sound using the multi-focus approach was not significantly different from the value obtained with a-priori knowledge of the sample thickness. The mean relative difference was ±1.3% (FIG. 14). In the range of porosity [0% to 19%], the cortical bone thickness was predicted with a mean relative error of 1.2% corresponding to 0.05 mm (FIG. 18). For all evaluations, the apodization factor was set to $k_{ap}$=0.9.

Following, results for estimation of cortical thickness and speed of sound in plexiform bovine bone are discussed.

Samples were cut to parallel sections of variable thickness to cover the approximate range of thickness values for human tibia bones. Thickness and speed of sound (SOS) reference values were obtained using a caliper and plane transducer through-transmission measurements. Table 1 below and FIGS. 27 and 28 show agreement between reference values (measured values) and those obtained using the multi-focus method as described above.

TABLE 1

| Sample ID | Caliper Thickness [mm] | Through Transmission SOS [m/s] | Multi-focus Thickness, mm | Multi-focus SOS, m/s |
|---|---|---|---|---|
| 1 | 1.61 ± 0.02 | 3524 ± 173 | 1.65 ± 0.08 | 3474 ± 208 |
|   |             |             | 1.75 ± 0.05 | 3640 ± 100 |
| 2 | 3.66 ± 0.04 | 3262 ± 68  | 3.37 ± 0.10 | 3057 ± 77 |
|   |             |             | 3.75 ± 0.15 | 3435 ± 236 |
| 3 | 4.63 ± 300.03 | 3340.8 ± 48 | 4.72 ± 0.05 | 3282 ± 56 |
|   |             |             | 4.85 ± 0.08 | 3291 ± 61 |
| 4 | 1.56 ± 0.01 | 3250 ± 160 | 1.64 ± 0.05 | 3386 ± 74 |
|   |             |             | 1.60 ± 0.05 | 3409 ± 115 |

Compared to X-ray methods, the present method may have the following advantages:

No exposure to ionizing radiation,
broad availability of imaging systems,
direct association of measured parameter with microstructural pore dimensions, i.e., pore diameters in the range between 30 and 80 μm, which are not resolved, even with the best in-vivo HRpQCT systems (in-vivo voxel size of the best system is 61 μm),
measurement possible at multiple skeletal sites
measurement of bulk sound velocity, which is related to matrix stiffness and porosity.

Compared to other QUS methods, the present method may have the following advantages:

no dedicated bone QUS hardware is required,
the use of a 3D-imaging system allows simple image guided control of probe positioning/repositioning and beam focusing prior to the measurement,
hardware more sophisticated and versatile compared to dedicated bone QUS systems,
soft tissue layer variations do not influence the analysis of the bone backscatter signals,
a single measurement acquires 3D multi-angle volumes of a representative cortical bone tissue volume (~100× 50×4 mm$^3$) and allows the evaluation of sub-volumes (estimated as small as 1×1×1 mm$^3$) instead of a bulk parameter,
the 3D data acquisition minimizes the operator dependence of the measurement,
direct association of the measured spectral parameter with microstructural tissue characteristics,
direct, independent, and simultaneous assessment of speed of sound and thickness of cortical bone, and
measurement of cortical bone properties at multiple physiologically relevant sites of bone remodeling.

Compared to any other in-vivo method targeting cortical bone, the proposed method can determine pore dimensions in the range between 30 μm and 80 μm, i.e., the range associated with a transition from normal to pathological bone remodeling.

The method can be applied for the in-vivo monitoring of early treatment response to novel drugs (to which BMD is rather insensitive), or to determine onset/duration of need for treatment of other pathologies affecting bone (e.g., dialysis, diabetes, sarcopenia, pediatric bone disorders, rare bone diseases) or medication side-effects (e.g., corticosteroid therapy, children treated with growth hormones). The method provides a cost-effective, non-ionizing, longitudinal diagnostic tool, which is sensitive to cortical microstructural properties. The present disclosure may be applied in the following applications: non-ionizing cost-effective diagnosis of osteoporosis and fracture risk, non-ionizing monitoring of bone health in pediatric patients, and/or monitoring cortical bone health for people at risk for fractures (high risk factors, prior to indication for BMD measurement). The easy-to-use, cost-effective and non-harmful method allows earlier diagnosis of the onset of bone pathologies and monitoring at shorter intervals thus reducing the number of new fragility fractures.

The features disclosed in the specification, the claims and the figures can be relevant for the realization of embodiments either alone or in any combination with each other.

The invention claimed is:

1. A system for determining characteristics of a cortical bone in a living body, comprising:
an ultrasound transducer array configured to transmit a multi-directional focused transmission of ultrasound waves to a region of interest that comprises the cortical bone in the living body, wherein the ultrasound transducers in the array are configured to scan a 3D volume by transmitting the multi-directional focused transmissions of ultrasound waves to the region of interest and to receive ultrasound waves which are backscattered from the region of interest; and
a processor coupled to the ultrasound transducer array configured to perform a depth-dependent spectral analysis of the backscattered ultrasound waves received due to the scans of the 3D volume, and to determine at least one of a pore size, pore number density, or porosity of the cortical bone based on the depth-dependent spectral analysis, wherein the ultrasound transducers array is further configured to provide a multidirectional and multi-focus transmission of ultrasound waves to the region of interest, and wherein the processor is further configured to perform spectral analysis of the backscattered ultrasound waves of the multidirectional and multi-focus transmission of ultrasound waves to the region of interest to determine a bone thickness of the cortical bone and a speed of sound in the cortical bone.

2. The system of claim 1, wherein the array is a one-dimensional array.

3. The system of claim 1, wherein the array is a two-dimensional array.

4. The system of claim 3, further comprising a control unit which is configured to control at least one of a position, a direction, a transmit frequency, and a focus depth of the ultrasound wave.

5. The system of claim 1, wherein the processor is to detect an outer bone surface of the cortical bone.

6. The system of claim 1, wherein the processor is to determine a reference spectrum from ultrasound waves backscattered at normal incidence.

7. The system of claim 1, wherein the processor is to calculate a depth-dependent normalized backscatter spectrum (248).

8. The system of claim 1, wherein the processor is to determine an apparent integrated backscatter (AIB) amplitude.

9. The system of claim 1, wherein the processor is to:
determine confocal positions (232, 252) and travel time delay of front and back-side reflections of the ultrasound wave for each of a plurality of scan positions; and
determine at least one of a speed of sound and a bone thickness using ultrasound refraction-based relationships.

10. The system of claim 1, wherein the ultrasound waves has a frequency from 1 MHz to 10 MHz.

11. The system of claim 1, wherein the processor is further configured to determine the pore size in the cortical bone with a pore diameter in a range of 30 μm to 80 μm.

12. The system of claim 1, wherein processor is configured to calculate the speed of sound in the cortical bone and the thickness of the cortical bone in the living body from a focus-dependent variation of amplitudes of bone front and back-side reflections and a pulse travel time delay between the amplitudes of bone front and back-side reflections.

13. A method for determining characteristics of a cortical bone in a living body, comprising:
performing, using an array of ultrasound transducers, scans of a 3D volume by transmitting multidirectional and multi-focus transmissions of ultrasound waves to a region of interest that comprises the cortical bone in the living body;
receiving, using the array of ultrasound transducers, ultrasound waves which are backscattered from the region of interest in response to the multidirectional and multi-focus transmissions of ultrasound waves to the region of interest;
performing a depth-dependent spectral analysis of the backscattered ultrasound waves received due to the scans of the 3D volume;
determining at least one of a pore size, pore number density, or porosity of the cortical bone based on the depth-dependent spectral analysis of the backscattered ultrasound waves; and
determining a bone thickness of the cortical bone and a speed of sound in the cortical bone based on the depth-dependent spectral analysis of the backscattered ultrasound waves.

14. The method of claim 13, further comprising calculating the speed of sound in the cortical bone and the thickness of the cortical bone from a focus-dependent variation of amplitudes of bone front and back-side reflections and a pulse travel time delay between the amplitudes of bone front and back-side reflections.

15. The method of claim 13, further comprising determining a reference spectrum from ultrasound waves backscattered at normal incidence.

16. The method of claim 13, further comprising calculating a depth-dependent normalized backscatter spectrum.

17. The method of claim 13, further comprising determining an apparent integrated backscatter amplitude.

18. A non-transitory computer readable medium comprising computer program product which, when executed by a processor, causes the processor to perform the following:
use an array of ultrasound transducers to perform scans of a 3D volume by transmitting multidirectional and multi-focus transmissions of ultrasound waves from the respective ultrasound transducers to a region of interest that comprises a cortical bone in a living body;
use the array of ultrasound transducers to receive ultrasound waves which are backscattered from the region of interest in response to the multidirectional and multi-focus transmissions of ultrasound waves to the region of interest; and
perform a depth-dependent spectral analysis of the backscattered ultrasound waves of the multidirectional and multi-focus transmission of ultrasound waves to the region of interest to determine at least one of a pore size, pore number density, or porosity of the cortical bone, and to determine a bone thickness of the cortical bone and a speed of sound in the cortical bone.

* * * * *